(12) United States Patent
Bartelmez et al.

(10) Patent No.: US 6,627,191 B1
(45) Date of Patent: Sep. 30, 2003

(54) ANTI-TRANSFORMING GROWTH FACTOR BETA (TGF-β) TREATED STEM CELL COMPOSITION AND METHOD

(75) Inventors: Stephen H. Bartelmez, Seattle, WA (US); Ewa Sitnicka, Lund (SE); Frank Ruscetti, New Market, MD (US)

(73) Assignee: Seattle Biomedical Research Institute, Seattle, WA (US)

( * ) Notice: Subject to any disclaimer, the term of this patent is extended or adjusted under 35 U.S.C. 154(b) by 0 days.

(21) Appl. No.: 09/490,520

(22) Filed: Jan. 25, 2000

Related U.S. Application Data

(60) Provisional application No. 60/117,219, filed on Jan. 25, 1999, and provisional application No. 60/117,217, filed on Jan. 25, 1999.

(51) Int. Cl.⁷ .............................. C12N 5/06; C12N 5/08
(52) U.S. Cl. ..................... 424/93.7; 435/325; 435/372; 435/375
(58) Field of Search ..................... 424/93.7; 435/325, 435/372, 375

(56) References Cited

U.S. PATENT DOCUMENTS

| | | | | |
|---|---|---|---|---|
| 5,061,620 A | * | 10/1991 | Tsukamoto et al. | 435/7.21 |
| 5,958,774 A | * | 9/1999 | Klein et al. | 435/455 |

FOREIGN PATENT DOCUMENTS

| | | | |
|---|---|---|---|
| WO | WO 94/18991 | | 9/1994 |
| WO | 96/19567 | * | 6/1996 |

OTHER PUBLICATIONS

Dasch, J. R. et al., "Monoclonal Antibodies Recognizing Transforming Growth Factor Beta", *J. Immunology—142*(5):1536–1541 (1989).

Herlyn, M. et al., "Growth–Regulatory Factors for Normal, Premalignant, and Malignant Human Cells In Vitro", *Adv. in Cancer Research—54*:213–234 (1990).

Wang, X. F. et al., "Expression Cloning and Characterization of the TGF–Beta Type III Receptor", *Cell—67*:797–805 (1991).

Jordan, C. T. et al., "Cellular and Development Proterties of Fetal Hematopoietic Stem Cells", *Cell—61*:953–963 (1990).

Waegell, W. O. et al., "Neutralizing Antibody to TGF–Beta Overcomes Normal Growth Controls in Long–Term Bone Marrow Cultures", *J. Cell. Biochem.—16*(c), Abstract NO. M342 (1992).

Fortunel, N. et al., "Release from Quiescenc of Primitive Human Hematopoietic Stem/Progenitor Cells by Blocking Their Cell–Surface TGF–Beta Type II Receptor in a Short-Term In Vitro Assay", *Stem Cells—18*(2):102–111 (2002).

Hatzfeld, A., et al., "Increaded Stable Retrovirol Gene Transfer in Early Hematopoietic Progenitkors Released from Quiescence" *Human Gene Therapy 7*:207–213 (1996).

Imbert, A.M., et al., "A neutralizing anti—TGF—β1 antibody promotes proliferation of $CD34^+Thy—1$ peripheral blood progenitors and increases the number of transduced progenitors" *Exper Hemat 26*:374–381 (1998).

Ploemacher, R. E., et al., "Autocrine Transforming Growth Factor $β_1$ Blocks Colony Formation and Progenitor Cell Generation by Hemopoietic Stem Cells Stimulated with Steel Factor" *Stem Cells 11*:336–347 (1993).

Sitnicka, E., et al., "Transforming Growth Factor $β_1$ Directly and Reversibly Inhibits the Initial Cell Divisions of Long—Term Repopulating Hematopoietic Stem Cells" *Blood 88*(1) : 82–88 (1996).

Soma , T., et al., "Maintenance of Murine Long—Term Repopulating Stem Cells in Ex Vivo Culture Is Affected by Modulation of Transforming Growth Factor—β But Not Macrophage Inflammatory Protein—1α Activities" *Blood 87*(11) :4561–4567 (1996).

Waegell, W. O., et al., "Growth acceleration and stem cell expansion in Dexter—type cultures by neutraliztion of TGF—β" *Exper Hemat 22*:1051–1057 (1994).

Yu, J., et al., "Abrogation of TGF—β activity during retroviral transduction improves murine hematopoietic progenitor and repopulating cell gene transfer efficiency" *Gene Therapy 5*:1265–1271 (1998).

* cited by examiner

*Primary Examiner*—David Saunders
(74) *Attorney, Agent, or Firm*—Heller Ehrman White & McAuliffe LLP

(57) ABSTRACT

The invention relates to stem cell compositions comprising anti-TGF-β treated stem cells which are viable for at least 14 days in culture without replication or differentiation and methods for rapid and long term in vitro hematopoiesis and in vivo hematopoietic reconstitution using such anti-TGF-β treated stem cells.

3 Claims, 4 Drawing Sheets

ANTI-TRANSFORMING GROWTH FACTOR BETA (TGF-β) TREATED STEM CELL COMPOSITION AND METHOD

This avtplication claims priority to U.S. Provisional application Serial No. 60/117,217 filed Jan. 25, 1999, and No. 60/117,219, filed Jan. 25, 1999 expressly incorporated by reference herein.

This work was supported in part by U.S. Government Agency and Government Grant No. R10 DK48708. Accordingly, the United States Government may have certain rights in this invention.

FIELD OF THE INVENTION

The present invention relates to stem cell compositions and methods for preparing them in vitro or ex vivo by culturing stem cells in medium containing anti-TGF-β antibodies in the absence of exogenously provided cytokines. Such treatment facilitates the survival of long term repopulating hematopoietic stem cells (LTR-HSC) within the culture for at least 14 days without replication or differentiation, the rapid engraftment of such LTR-HSC following in vivo administration to a mammal or the rapid proliferation of such LTR-HSC following transfer to in vitro culture conditions effective to result in such expansion.

BACKGROUND OF THE INVENTION

The hematopoietic stem cell (HSC) is a pluripotent progenitor cell that has been characterized as a cell that is transplantable, can self-replicate or generate daughter cells that are destined to commit to mature cells of different specific lineages.

Self-replication of the most primitive HSC produces daughter cells that possess a long (possibly unlimited) clonal lifespan, while differentiation of HSCs results in a loss of such multilineage potential, and corresponding lineage commitment with a progressive reduction of their clonal lifespan. Previous studies indicated that survival of HSC ex vivo in the absence of growth factors is limited, resulting in a complete loss of HSC after about 0.5–4 days in culture (Bartelmez S, unpublished data; Ploemacher R E et al. Stem Cells 11:336–347, 1993; Li and Johnson, Blood 15;84(2):408–14, 1994).

Transplantation studies have shown that a single HSC can repopulate the marrow of a lethally irradiated mouse, demonstrating that self-renewal of HSC occurs in vivo, as indicated by transplantation studies wherein a single HSC repopulated the marrow of an immunodeficient mouse (Smith, L G et al., *Proc Natl Acad Sci USA* 88, 2788–92, 1991: Osawa M et al., *Science* 273, 242–245, 1996). In addition, repopulation of secondary (and tertiary) recipients, has been demonstrated (Dick J E et al *Cell* 42, 71–9, 1985; Jordan C T et al., *Genes Dev* 4, 220–32, 1990; Keller G and Snodgrass R *J Exp Med* 171, 1407–18, 1990).

Transforming growth factor beta-1 (TGF-β1) is known to directly and reversibly inhibit the initial cell divisions of long-term repopulating hematopoietic stem cells (LTR-HSC) in vitro. (See, e.g., Sitnicka E et al, *Blood,* 88(1):82–88, 1996 and Ploemacher R E et al., *Stem Cells* 11(4):336–47, 1993.) The in vivo administration of TGF-β to humans to enhance the number of hematopoietic progenitor cells in peripheral blood has also been described. (See, e.g. U.S. Pat. No. 5,674,843, issued Oct. 7, 1997.) The mode of action of the observed pleiotrophic effect of TGF-β on stem and progenitor cells has been attributed to TGF-β as an inhibitor of cell proliferation or a mediator of apoptosis.

Murine marrow cells treated with anti TGF-β antibody together with IL-3, IL-6 and stem cell factor demonstrated a greater retroviral transduction efficiency of progenitor (CFU-C) and long-term repopulating cells than cells treated with IL-3, IL-6 and stem cell factor alone (Yu J et al., Gene Ther 5(9):1265–71, 1998).

Extensive studies have been described wherein HSC are cultured in the presence in various combinations of cytokines as a means to increase the number of HSC. In general, such culture conditions have caused differentiation of HSC and do not result in survival or increased numbers of viable long term repopulating HSC (Li and Johnson, Blood 15;84(2):408–14, 1994; Peters S O et al., Blood. 87(1):30–7. 1996; Yonemura Y et al., *Proc Natl Acad Sci USA.* 93(9):4040–4. 1996).

High-dose chemotherapy and/or radiation therapy together with bone marrow transplantation or transplantation of a cell population enriched for hematopoietic stem cells are standard treatment regimens for some malignancies, including, acute lymphocytic leukemia, chronic myelogenous leukemia, neuroblastoma, lymphoma, breast cancer, colon cancer, lung cancer and myelodysplastic syndrome, as well as for other non-malignant hematopoietic diseases, e.g. thrombocytopenia. Such treatments have shown promise in effective elimination of several types of cancer, however in all cases the high doses also destroy bone marrow stem cells. In addition, bone marrow transplantation may play a major role in the emerging field of gene therapy.

Clinical trials are underway using such regimens for the treatment of various cancers, including ovarian cancer, thymomas, germ cell tumors, multiple myeloma, melanoma, testicular cancer, lung cancer, and brain tumors.

In addition, HSC have been demonstrated to be capable of repopulating non-hematopoietic tissues, including but not limited to liver (Petersen B E et al., Science 284:1168–70, 1999) and neuronal tissue (Bjornson C R R et al., Science 283:534–7, 1999).

Cell preparations enriched for hematopoietic stem cells generally contain a low percentage of cells capable of long-term hematopoietic reconstitution. In general, culture conditions effective to promote the survival of hematopoietic stem cells include cytokines, which stimulate cell division and differentiation of the cells, diminishing their long term repopulating capability. Frequently, as a result, in vivo administration of such cell preparations does not result in rapid repopulation of the host hematopoietic system. In particular, the slow repopulation of the neutrophil and platelet compartments of the hematopoietic system may result in susceptibility to infection and/or complications due to poor blood clotting. In addition, once isolated, stem cell preparations are typically frozen in liquid nitrogen for subsequent use and upon thawing the number of viable stem cells is further reduced.

Therefore, a need remains to develop techniques for maintaining stem cells in culture and for the use of such cells in both rapid and long-term hematopoietic reconstitution.

SUMMARY OF THE INVENTION

The present invention addresses two significant problems in the field of stem cell transplantation. As known in the art, hematopoietic stem cells capable of long term repopulation in vivo generally do not survive in culture without cell division, which usually results in differentiation of the cells out of the stem cell compartment. In addition, the time required for in vivo repopulation of the hematopoietic system of a subject following in vivo administration of such stem cells is sufficiently long that passive administration of platelets and neutrophils is often required to ensure the survival of the patient.

The present invention provides a composition of anti TGF-β antibody-treated stem cells capable of stivival for at least 14 days in vitro or ex vivo with continuous anti TGF-β antibody treatment and a method for obtaining the same.

The anti TGF-β antibody-treated stem cell compositions of the invention provide a source of stem cells for rapid and sustained repopulation of the hematopoietic system of the subject. The compositions of the present invention provide a number of advantages relative to currently available stem cell preparations including: (1) hematopoietic repopulation which takes place at least 2-fold more rapidly following in vivo administration; (2) hematopoietic repopulation in vivo with a minimal number of cells, e.g., at least 10-fold fewer stem cells if antibody-treated (3) sustained repopulation of the hematopoietic system of the subject for a clinically useful time; (4) stem cell proliferation in vitro which takes place at least 2-fold more rapidly following transfer to culture conditions effective to promote such proliferation; (5) stem cell proliferation in vitro with a minimal number of cells, e.g., at least 10-fold fewer stem cells if antibody-treated; and (6) sustained stem cell proliferation in vitro resulting in generation of various lineages of hematopoietic cells for at least six months.

In one preferred aspect of the invention, the stem cells are human hematopoietic stem cells, characterized as lacking the expression of lineage markers (lin-), and either (a) positive for cell surface expression of CD 34 and KDR and negative for cell surface expression of CD38 or (b) positive for cell surface expression of both CD 34 and Thy1.

In another aspect, the culture conditions effective to preserve the viability and differentiation state of said stem cells include culture medium which contains from about 0.5 to 100 μg/ml of anti TGF-β antibody and lacks exogenously provided cytokines.

The invention further provides a method of obtaining a stem cell composition characterized by prolonged survival in culture which includes the steps of obtaining a population of cells enriched for stem cells and exposing the stem cells, ex vivo, to an anti TGF-β antibody, under culture conditions, and for a period of time, effective to preserve the viability and differentiation state of the cells.

A method for rapid in vivo repopulation of the hematopoietic system of a subject and a method for rapid proliferation of a stem culture in vitro are further provided by the invention. Such methods include the steps of obtaining a population of cells enriched for stem cells and exposing the stem cells, ex vivo, to an anti TGF-β antibody, under culture conditions, and for a period of time, effective to preserve the viability and differentiation state of the cells, followed by either (a) readministering the anti TGF-β antibody treated stem cells to the subject or (b) transferring the anti TGF-β antibody treated stem cells to culture conditions effective to result in the rapid proliferation of the cells, for in vivo and in vitro applications, respectively.

These and other objects and features of the invention will become more fully apparent when the following detailed description is read in conjunction with the accompanying figures and examples.

DETAILED DESCRIPTION OF THE INVENTION

I. Definitions

Figure 1:
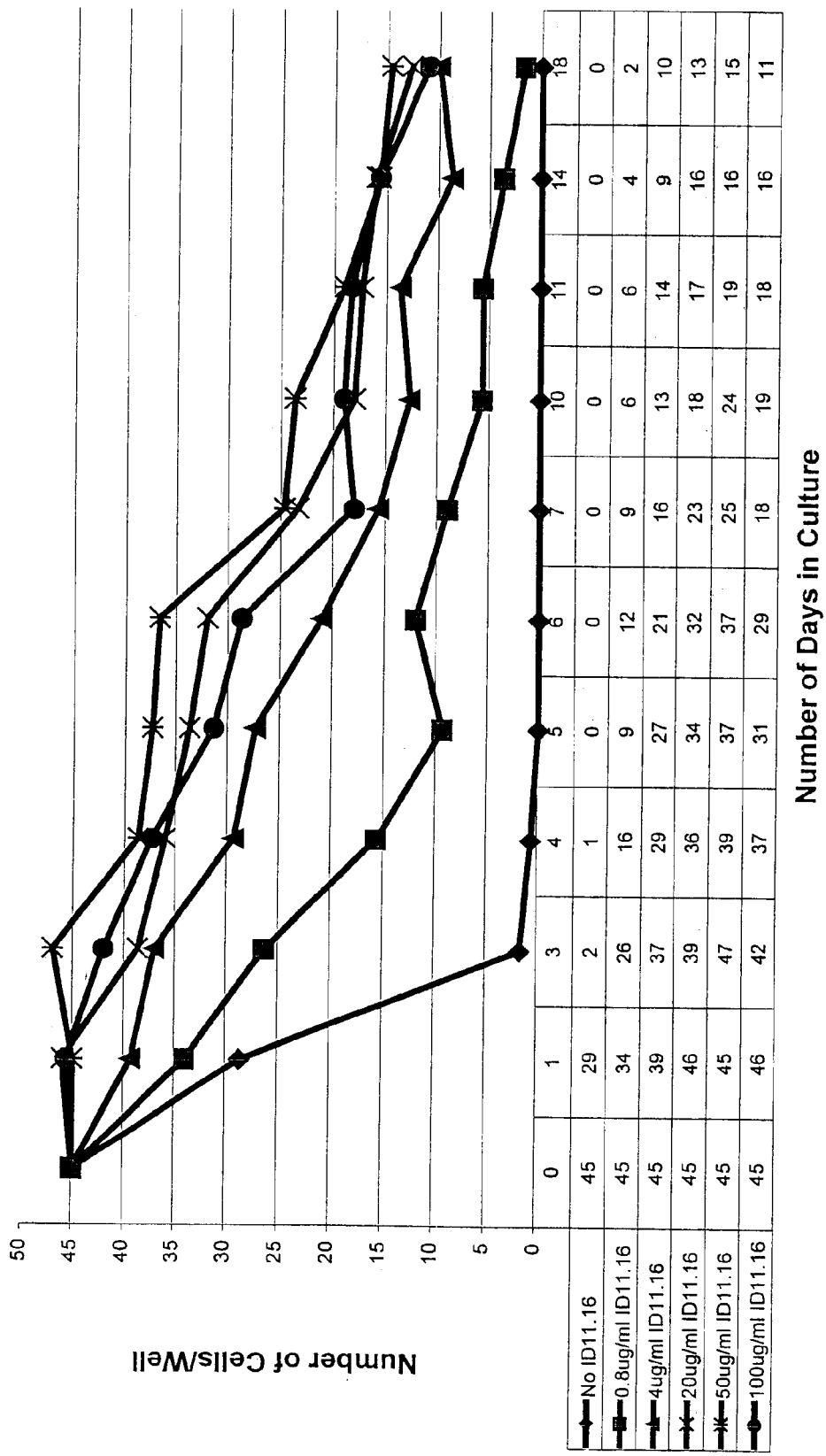
FIG. 1 illustrates the survival of single sorted LTR-HSC in the presence of anti-TGF-β1 antibody as indicated by the number of HSC per well as counted on day 0, 1, 3, 4, 5, 6, 7, 10, 11, 14, 18 when incubated in medium alone or medium containing 0.8–100 μg/ml of TGF-β1 neutralizing antibody, ID.11.16.

The terms below, as used herein, have the following meanings, unless indicated otherwise:

As used herein, the term "a cell population enriched for hematopoietic stem cells" refers to a cell population obtained using the positive and negative selection techniques described herein, wherein the hematopoietic stem cells are LTR- or STR-HSCs.

As used herein, the terms "HSC expansion" and an "increased number of HSC" refer to an increase in the number of LTR-HSC and STR-HSC.

As used herein, the terms "stem cell expansion" and an "increased number of stem cells" refer to an increase in the number of stem cells which are not necessarily HSC.

As used herein, "long term repopulating hematopoietic stem cells" or "LTR-HSC", refers to hematopoietic stem cells that are transplantable, and contribute to all lineages of hematopoietic cells for an undefined period of time, when transplanted into totally immunosuppressed recipients and do not undergo clonal extinction, as exemplified herein by murine LTR-HSC. The long term repopulating ability of candidate hematopoietic stem cells may be evaluated in an in vivo sheep model or an in vivo NOD-SCID mouse model for human HSC and normal immunosupressed mice for murine HSC, respectively, as further described herein.

LTR-HSC have been isolated and characterized in mice using fluorescence-activated cell sorter (FACS) selection of density gradient-enriched, lineage-depleted bone marrow cells which are negative for expression of the CD34 antigen, positive for expression of the CD117 (c-kit) antigen, and exhibit low-level binding of the DNA binding dye, Hoechst 33342 (Ho-33342) and the mitochondrial binding dye, Rhodamine 123 (Rh-123), (Wolf, et al., 1993). The isolated cell population was demonstrated to be transplantable and capable of repopulating lethally irradiated recipients, when transplanted together with unfractionated bone marrow cells.

As used herein, the term "short term repopulating hematopoietic stem cells" or "STR-HSC", refers to murine hematopoietic stem cells that are transplantable and contribute to all lineages of hematopoietic cells for a period of from about one week to 6 months, then undergo clonal extinction. The STR-HSC population may be selected by FACS sorting and are phenotypically defined as light density gradient-enriched bone marrow cells which lack the expression of lineage markers (lin-), are positive for c-kit (CD 117), Sca1 and CD34, exhibit low-level binding of the DNA binding dye, Hoechst 33342 (Ho-33342) and high-level binding of the mitochondrial binding dye, Rhodamine 123 (Rh-123).

The term "clonal extinction", as used herein refers to the terminal differentiation of a single hematopoietic stem cell and all the progeny produced by clonal expansion of that cell, such that no more daughter cells are produced from the initial clone.

The term "pluripotent hematopoietic stem cells" refers to hematopoietic stem cells, capable of differentiating into all the possible cell lineages.

As used herein, the term "high proliferative potential colony forming cells" or "HPP-CFCs", as used herein relative to hematopoietic stem cells refers to murine or human cells that proliferate in response various cytokines and other culture conditions. By way of example, murine HPP-CFC are produced by culture of murine HSC in the presence of rat rSCF, mouse rIL-3 and human rIL-6. The cells proliferate in semi-solid media, such as agar or methyl cellulose or as single cells in liquid culture, and form macroclones which have a diameter greater than 1 mm, generally having greater than 100,000 cells per clone with dense multicentric centers. This population includes all murine HSCs, however, not all HPP-CFC are HSCs, and the HPP-CFC assay is not a specific assay for LTR-HSC. In contrast, low proliferative potential (LPP) clones contain from 2 to 100,000 cells per clone.

As used herein, "lineage-committed hematopoietic stem cells" are hematopoietic stem cells that have differentiated sufficiently to be committed to one or more particular cell lineages, but not all cell lineages.

As used herein, the term "lin-" or "lineage-depleted", refers to a cell population which lacks expression of cell surface antigens specific to T-cells, B-cells, neutrophils, monocytes and erythroid cells, and does not express antigens recognized by the "YW 25.12.7" antibody. (See, e.g., Bertoncello I et al., *Exp Hematol* 19(2):95–100, 1991.)

As used herein, the terms "develop", "differentiate" and "mature" are used interchangeably and refer to the progression of a cell from a stage of having the potential to differentiate into multiple cellular lineages to becoming a more specialized cell committed to one or more defined lineages.

As used herein, the term "purified", relative to hematopoietic stem cells refers to HSCs that have been enriched (isolated or purified) relative to some or all of the other types of cells with which they are normally found in a particular tissue in nature, e.g., bone marrow or peripheral blood. In general, a "purified" population of HSCs has been subjected to density gradient fractionation, lineage depletion and positive selection for c-kit and Sca-1 expression in addition to low level staining with both Hoechst 33342 and Rhodamine 123.

As used herein, a population of cells is considered to be "enriched" for human HSC if greater than 0.1% of the CD 34+ cells have an immunophenotype characteristic of human HSC, e.g., CD34+ CD38-KDR+; or CD34+ Thy1+.

As used herein, the term "hematopoietic cells", refers to the types of cells found in the peripheral blood which are typically assayed as indicators of hematopoietic reconstitution and includes platelets, neutrophils, B lymphocytes and T lymphocytes.

As used herein, the terms "in vivo repopulation" and "in vivo reconstitution" refer to an absolute neutrophil count in the peripheral blood which is greater than 500/μL and an absolute platelet count which is greater than 30,000/μl. It follows that "time to repopulation" and "time to reconstitution" refer to the amount of time following in vivo administration of a cell preparation until the time that the absolute neutrophil count in the peripheral blood is greater than 500/μl and the absolute platelet count is greater than 30,000/μl.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

As used herein "treatment" of an individual or a cell is any type of intervention used in an attempt to alter the natural course of the individual or cell. Treatment includes, but is not limited to, administration of e.g., a cellular or pharmaceutical composition, and may be performed either prophylactically, or subsequent to the initiation of a pathologic event or contact with an etiologic agent.

As used herein, the term "improved therapeutic outcome" relative to a cancer patient refers to a slowing or diminution of the growth of cancer cells or a solid tumor, or a reduction in the total number of cancer cells or total tumor burden.

II. Hematopoietic Stem Cell Compositions

Cytokines

Recently, combinations of cytokines, including stem cell factor (SCF, or c-kit ligand), thrombopoietin (Tpo, c-mpl ligand), and the ligand for the Flt3/Flk2 receptor (FL), have been shown to act directly on HSC (Ogawa M et al., *Stem Cells* 15 Suppl 1, 7–11, 1997; Ku H et al., *Blood* 87, 4544–51, 1996; Ramsfjell V et al., *Blood* 88, 4481–92, 1996; Sitnicka E et al., *Blood* 87, 4998–5005, 1996; Young J C et al., *Blood* 88, 1619–31, 1996; Yoshida M et al., *Br J Haematol* 98, 254–64, 1997; Matsunaga T et al., *Blood* 92, 452–61, 1998). In addition, Tpo as a single growth factor has been demonstrated to support survival and modest proliferation of highly purified HSC in vitro (Ramsfjell V et al., *Blood* 88, 4481–92, 1996; Sitnicka E et al., *Blood* 87, 4998–5005, 1997).

TGF-β, Anti TGF-β Antibodies and Stem Cells

TGF-β1 has been shown to directly and reversibly inhibit the initial cell divisions of murine long-term repopulating hematopoietic stem cells (LTR-HSC) in vitro (Sitnicka E et al, *Blood* Jul. 1, 1996;88(1):82–88). It follows that blocking the effects of TGF-β would be expected to promote such initial cell divisions. However, the various literature references directed to the effect of TGF-β and anti-TGF-β antibodies on HSC do not provide consistent results. For example, the administration of TGF-β to humans has been described as capable of enhancing the number of hematopoietic progenitor cells in the peripheral blood. (See, e.g. U.S. Pat. No. 5,674,843, issued Oct. 7, 1997.) In other references the effect of TGF-β on stem and progenitor cells has been described as inhibition of cell proliferation or mediation of apoptosis, based on the demonstration that if LTR-HSC were cultured with greater than 0.1 ng/ml TGF-β1 (plus hematopoietic growth factors [HGF]), the probability of the maintenance or expansion of HPP daughter cells appeared to increase (Sitnicka E et al, *Blood* Jul. 1, 1996;88 (1):82–88). It was further observed that when a neutralizing anti-TGF-β1 monoclonal antibody was added with c-kit ligand or IL-3 to the cells, the proportion of LTR-HSC that divided increased as well as did the average clone size (Sitnicka E et al, 1996).

Various references to culture of hematopoietic cells in the presence of anti TGF-β antibodies may be found in the literature. The recited culture conditions vary considerably, however, in general the references describe bone marrow cells or stem cell-enriched cell preparations cultured under conditions which include combinations of cytokines.

In one example, TGF-β was added to ex vivo cultures of murine stem cells. containing interleukin-3 (IL-3), IL-6, and stem cell factor (SCF) was shown to suppress short- and long-term repopulating activity in a murine competitive repopulation assay. An anti TGF-β neutralizing antibody, reversed such effects relative to control cultures containing IL-3, IL-6, and SCF alone (Soma T et al., Blood Jun. 1, 1996;87(11):4561–7).

Several other references describe murine marrow cells treated with anti TGF-β antibody together with various cytokines, e.g., IL-3, IL-6 and stem cell factor, wherein a greater retroviral transduction efficiency was observed in progenitor (CFU-C) and long-term repopulating cells relative to cells treated with IL-3, IL-6 and stem cell factor alone. (See, e.g., Yu J et al., Gene Ther September 1998;5(9):1265–71).

In another example, Dexter-type long-term murine bone-marrow cultures were treated with a monoclonal antibody that neutralizes the biological activity of TGF-β resulting in at least three times as many stem cells as control cultures (Waegell W O et al., Exp HematolOctober 1994;22(11):1051–7).

Improved gene transfer into human hematopoietic progenitor cells prestimulated with cytokines was demonstrated when the effect of TGF-β1 was blocked by antisense or antiserum to release stem cells from quiescence. (See, e.g., Hatzfeld et al., 1991, *J. Exp. Med.,* 174, 925; Hatzfeld A et al. *Hum Gene Ther* Jan. 20, 1996;7(2):207–13; Imbert A M et al., *Exp Hematol* May 1998;26(5):374–81; and U.S. Pat. No. 5,958,774.)

Such experiments are generally directed to releasing stem cells from quiescence (i.e., causing them to enter the cell cycle and to differentiate).

Numerous anti TGF-β antibodies are described in the literature and many are commercially available. Table 1, below provides background information on representative anti TGF-β antibodies and a summary of the effect of each antibody on support for stem cell survival; the ability of HSC treated with the antibody to induce rapid repopulation upon transfer in vivo or upon in vitro culture under conditions which promote HSC differentiation; the ability of HSC treated with the antibody to induce sustained repopulation upon such in vivo transfer or in vitro culture.

containing the anti TGF-β antibody and lacking exogenously provided cytokine Such anti TGF-β antibody-treatment is effective to result in (1) stem cell survival in vitro at 37° C. or 4° C. for at least 14 days, (2) rapid hematopoietic repopulation following in vivo administration of antibody-treated stem cells, (3) induction of sustained repopulation following in vivo administration; (4) rapid stem cell proliferation in vitro following transfer to culture conditions effective to promote such proliferation; (5) stem cell proliferation in vitro with a minimal number of cells; and (6) sustained stem cell proliferation in vitro resulting in generation of various lineages of hematopoietic cells.

Such anti TGF-β antibody-treated stem cells therefore maintain the ability to provide long term sustained hematopoietic reconstitution (in vitro and in vivo), and also exhibit the capability of short term in vitro and in vivo repopulation, a quality which untreated stem cells do not possess.

It will be understood that any anti TGF-β antibody which exhibits the above-described characteristics finds utility in the methods and compositions of the invention and that the invention is not limited to the specific antibodies included in the examples described herein.

It will also be understood that any anti-stem cell antibody which exhibits the above-described characteristics finds utility in the methods and compositions of the invention and that the invention is not limited to the anti TGF-β antibodies described herein.

The conditions for prolonged stem cell survival in vitro presented herein as 37° C. or 4° C. for at least 14 days, are an example of typical culture conditions used by those of skill in the art to culture stem cells. The methods described herein are not limited to such conditions and the present invention includes stem cell treatment with anti TGF-β antibodies at any temperature which results in anti TGF-β antibody-facilitated survival of the cells.

Such antibodies may include, but are not limited to, polyclonal, monoclonal, chimeric, humanized, single chain, Fab fragments and fragments produced by an Fab expression library. Antibodies, i.e., those which block the biological

TABLE 1

Monoclonal antibodies for treatment of HSC[1].

| Monoclonal Antibody | Immunogen | Supportive of LTR-HSC survival | Ab-treated HSC induce rapid repopulation | Ab-treated HSC induce sustained repopulation | Ab specificity |
|---|---|---|---|---|---|
| ID11.16 | Bovine TGF-β2 | ++++ | ++++ | ++++ | TGF-β1, TGF-β2 |
| 12H5 | Human TGF-β1 | ++ | +++ | ++++ | TGF-β1 |
| 2G7 | Human TGF-β1 | No | +++ | +++ | TGF-β1, TGF-β2, TGF-β3 |
| 3C7.14 | Human TGF-β2 | No | +/− | +++ | TGF-β2 |
| 20724 | Human TGF-β3 | No | +++ | +/− | TGF-β3 |
| IgG1K Isotype | N/A | − | +/− | +/− | None |
| No treatment | N/A | − | +/− | +/− | N/A |

[1]As presented in Table 1, ++++ refers to a response which is greater than a response indicated as +++, which is greater than a response indicated as ++ and +/− refers to a result which reflects low, but measurable activity in the assay.

The results presented in Table 1 indicate the characteristics of an anti TGF-β antibody for use in the compositions and methods described herein. Such characteristics include, specific immunoreactivity with TGF-β, preferably TGF-β1 or TGF-β2, and the ability to modify stem cells following exposure of the cells for at least 20 minutes to medium effect of TGF-β on HSC, are especially preferred. See, e.g., Antibodies: A Laboratory Manual, Cold Spring Harbor Laboratory, 1988, expressly incorporated herein by reference herein.

Human or humanized antibodies are preferred for in vivo applications and for treatment of cells to be readministered in vivo due to the lack of potential for side effects which often result from an immune response to the antibody itself.

In one approach, transgenic animals (e.g. xenomice) may be produced which are capable, upon immunization, of producing a full repertoire of human antibodies in the absence of endogenous immunoglobulin production. In this approach, large fragments of both the human heavy and light chain Ig genes have been inserted into the mouse germline to create a mouse strain capable of producing a broad repertoire of antigen-specific, fully human antibodies.

The xenomouse produces B cells expressing human heavy chain (h mu) and human K light chain (h K), or h mu and mouse lambda (m lambda) light chain. These mice produce significant quantities of fully human antibodies with a diverse adult-like repertoire and, upon immunization with antigens, generate antigen-specific fully human monoclonal antibodies. (See, e.g., Jakobovits, A, et al., Ann N Y Acad Sci 764:525–35, 1995; Jakobovits, A, Curr Opin Biotechnol 6(5):561–6, (1995).

Such xenogenic mouse-derived human monoclonal antibodies may not have the correct Ig heavy chain for complement fixation in humans, e.g., IgG1. In such cases, the antibody encoding mRNA from the xenogenic mouse hybridoma may be used to obtain cDNA into which the appropriate cDNA for the IgG1 heavy chain is inserted. This cassette may then be inserted into an expression vector using procedures routinely employed by those of skill in the art, and subsequently for used in the production of transgenic goats. Transgenic goats have been developed wherein inducible promoters can trigger the expression of the protein encoded therein such that it is secreted into the milk of the goats. This procedure allows for relatively low cost production of large quantities of human monoclonal antibodies.

In one preferred embodiment, the anti-TGF-β monoclonal antibodies of the invention comprise humanized antibodies or human antibodies.

Alternative methods of blocking the biological effects of proteins are known in the art and fall within the scope of the present invention. For example, antisense oligonucleotides are frequently used to control gene expression through complementary polynucleotides, i.e. antisense DNA or RNA, to the control, 5' or regulatory regions of the gene encoding TGF-β. For example, the 5' coding portion of the polynucleotide sequence which codes for the protein of the present invention is used to design an antisense oligonucleotide of from about 10 to 40 base pairs in length. Oligonucleotides based on the transcription start site, e.g. between positions −10 and +10 from the start site, are preferred and the antisense DNA oligonucleotide is designed to be complementary to a region of the TGF-β gene involved in transcription [Lee, et al., Nucl. Acids Res. 6:3073 (1979); Cooney, et al., Science 241:456 (1988); and Dervan, et al. Science 251:1360 (1991)], thereby interfering with or preventing transcription and the subsequent production of TGF-β. Accordingly antisense oligonucleotides effective to block the expression of TGF-β, preferably uncharged antisense oligomers with modified (e.g., non-phosphodiester backbones) may be used in practicing the invention described herein.

Methods of Obtaining Hematopoietic Stem Cells

In adults, the large majority of pluripotent hematopoietic stem cells are found in the bone marrow. However, small but significant numbers of such cells can be found in the peripheral circulation, liver, spleen and cord blood.

Human hematopoietic stem cells for use in the present invention may be derived from human bone marrow, human newborn cord blood, fetal liver or adult human peripheral blood, after appropriate mobilization.

The frequency of hematopoietic stem cells can be dramatically increased by treatment of a subject with certain compounds including cytokines. Such "mobilized" peripheral blood hematopoietic stem cells have become an important alternative to bone marrow-derived hematopoietic stem cells transplantation procedures primarily because engraftment is more rapid. (See, e.g., Tanaka, J, et al., Int J Hematol 69(2):70–4, 1999.)

Such mobilization may be accomplished using for example, one or more of granulocyte colony-stimulating factor (G-CSF), stem cell factor (SCF), thrombopoietin (Tpo), and a chemotherapeutic agent (i.e., cyclophosphamide).

Numerous methods for human hematopoietic stem cell enrichment/isolation are known in the art and generally include obtaining bone marrow, newborn cord blood, fetal liver or adult human peripheral blood which contains hematopoietic stem cells. Once obtained, a hematopoietic stem cell population may be enriched by performing various separation techniques such as density gradient separation, immunoaffinity purification using positive and/or negative selection by panning, FACS or magnetic bead separation. Following such enrichment steps, the cell population is further characterized phenotypically and functionally.

Previous studies have also demonstrated that primitive hematopoietic cells, characterized as high proliferative potential colony-forming cells (HPP-CFC, in vitro) may be isolated by selecting a fraction of density gradient-enriched, lineage-depleted marrow cells, further selecting a cell population based on a single step fluorescence-activated cell sorter (FACS) fractionation for cells that bound low levels of the DNA binding dye, Hoechst 33342 (Hoechst$^{lo}$) and low levels of the mitochondrial binding dye, Rhodamine 123 (Rho$^{lo}$; Wolf NS et al., Exp Hematol 21(5):614–22, 1993).

In one exemplary enrichment method, normal murine marrow cells are processed using two pre-enrichment steps based on density gradient centrifugation (e.g., using Nycodenz 1.080 g/ml, Nygaard, Oslo, Norway), followed by negative selection using Dynal beads coupled to myeloid and lymphoid specific monoclonal antibodies and positive selection by FACS sorting of cells based on staining with Rhodamine 123 (Rh), Hoescht 3342(Ho) and antibodies to c-kit.

Once obtained, such candidate HSC may be characterized in a variety of in vitro and in vivo assays generally known in the art, as further described below. Such assays include, but are not limited to, an HPP-CFC assay, a single-cell HPP daughter cell assay, a single-cell IL-3 response assay, a single-cell assay for time to the first cell division, a cobblestone area-forming cell assay and an in vivo limiting dilution transplant assay to quantitate STR- and LTR-HSC.

Recently, it has been shown that a defined subpopulation of murine HPP-CFC are transplantable and that a subpopulation of the cells that give rise to HPP-CFC are LTR-HSCs, which can replicate ex vivo, as shown by the results of in vitro LTBMC and in vivo repopulation studies. (See, e.g., Yagi M et al., Proc. Nat. Acad. Sci. 96:8126–8131, 1999).

Culture/Function of Hematopoietic Stem Cell Compositions

Hematopoietic stem cells have been historically defined as transplantable cells, capable of self-renewal which possess the ability to generate daughter cells of any hematopoietic lineage. Lineage-committed progenitor cells are defined as more differentiated cells derived from hematopoietic stem cells.

The phenotypic markers which characterize the hematopoietic stem cell have been the subject of extensive debate and numerous publications. As yet, there is no consensus as to which markers are definitive for murine or human hematopoietic stem cells, however, the markers for LTR-HSC and STR-HSC, as used herein, are provided above.

Functional readouts that have been used to detect and characterize hematopoietic stem cells include the ability to form colonies under particular conditions in cell culture (in vitro), such as in the long term culture initiating cell (LTCIC) assay (Pettengell R et al., Blood 84(11):3653–9, 1994), long term bone marrow culture (LTBMC; Dexter T M et al., *Prog Clin Biol Res* 148, 13–33, 1984) and the high proliferative potential-colony-forming cell (HPP-CFC) assay. (See, e.g., Yagi M, et al., *Proc. Nat. Acad. Sci.* 96:8126–8131, 1999.) Further functional characterization includes in vivo assay for long-term repopulating hematopoietic stem cells (LTR-HSC) and short-term repopulating hematopoietic stem cells (STR-HSC), as further described below.

LTBMC (Dexter T M et al., 1984) develop a complex adherent stromal layer containing a large variety of cell types, and can generate nonadherent (NA) hematopoietic cells for periods of several months. Hematopoietic stem cells are also often characterized functionally by activity in the high proliferative potential colony-forming cell (HPP-CFC) assay, as defined above.

HPP-CFC are generally characterized by: (1) a relative resistance to treatment in vivo with the cytotoxic drug 5-fluorouracil; (2) a high correlation with cells capable of repopulating the bone marrow of lethally irradiated mice; (3) their ability to generate cells of the macrophage, granulocyte, megakaryocyte and erythroid lineages, and (4) their multifactor responsiveness. (See, e.g., McNiece, I. K., *Int J Cell Cloning* 8(3): 146–60, 1990).

Murine HSC

Preferred cytokines for the culture of murine hematopoietic stem cells include one or more of interleukin-3 (IL-3), interleukin-6 (IL-6), interleukin-11 (IL-11), interleukin-12 (IL-12), stem cell factor (SCF), fms-like tyrosine kinase-3 (flt-3), transforming growth factor-$\beta$ (TGF-$\beta$), an early acting hematopoietic factor, described, for example in WO 91/05795, and thrombopoietin (Tpo).

Long-term reconstitution of mice with murine LTR-HSCs following complete immunosuppression has been shown to require the transplantation of unfractionated bone marrow cells together with less differentiated long term repopulating cells, in order to provide initial, albeit unsustained engraftment, such that the completely immunosuppressed host may survive until the long term repopulating cells differentiate sufficiently to repopulate the host. (See, e.g., Jones, R. J., et al., *Nature* 347(6289):188–9, 1990). LTR-HSCs may take several months to effectively repopulate the hematopoietic system of the host following complete immunosuppression.

Methods have been developed to distinguish the cells of the donor and recipient in murine hematopoietic reconstitution studies, by using donor hematopoietic stem cells, congenic at the CD45 locus, defined as CD45.1 and recipient hematopoietic stem cells defined as CD45.2, such that monoclonal antibodies may be used to distinguish donor and recipient cells, i.e., by FACS analysis and/or sorting. In such detection methods, the recipient is infused with sufficient CD45.2 positive bone marrow cells to keep the mouse alive until differentiation of CD45.1 donor cells occur to an extent sufficient to repopulate the hematopoietic system of the recipient. Such methods may be used to differentiate LTR-HSC from STR-HSC and donor cells from recipient cells.

Human HSC

Human HSC are initially characterized by immunophenotype, e.g., as lineage negative and either (1) CD34+/Thy1+ or (2) CD 34+/CD38– cells that are also KDR+. Human HSC may also be characterized by telomere length, where cells with high proliferative capacity have longer telomeres. In general, a population of cells is considered to be enriched for human HSC if greater than 0.1% of the CD 34+ cells have the immunophenotype, CD 34+ CD38– KDR+ or CD34+ Thy1.

Preferred cytokines for the culture of human hematopoietic stem cells include one or more of interleukin-3 (IL-3), interleukin-6 (IL-6), interleukin-11 (IL-11), interleukin-12 (IL-12) stem cell factor (SCF), fms-like tyrosine kinase-3 (flt-3), transforming growth factor-$\beta$ (TGF-$\beta$), an early acting hematopoietic factor, described, for example in WO 91/05795, and thrombopoietin (Tpo).

Human adult hematopoietic stem cells are mostly quiescent or slow cycling. However, it has been demonstrated that when human stem cells are cultured under conditions which include exogenously provided cytokines, wherein TGF-$\beta$1 is blocked; quiescent, hematopoietic multipotent progenitors grow in a short term culture assay in which the cells do not grow when TGF-$\beta$1 is not blocked.

III. Treatment of Murine HSC with Anti TGF-$\beta$ Antibodies

Greater than 90% of single sorted murine LTR-HSC (lineage neg., $Rh^{low}$, $Ho^{low}$, c-kit +, Sca-1+) have been shown to form high proliferative potential (HPP) clones in the presence of SCF, IL-3, and IL-6 (Sitnicka E et al., *Blood* 87:4998–5005, 1996). In addition, such studies have indicated that essentially 100% of purified HSC cultured as single cells undergo their first cell division if specific hematopoietic cytokine combinations are present, e.g., SCF (c-kit ligand) plus IL-6, IL-11, IL-12, or IL-3 (Sitnicka et al. 1996).

LTR-HSC have also been shown to express either an active cell surface form and/or an active secreted form of TGF-$\beta$1 (Lucas C et al., J. Immunol., 145:1415–1422, 1990). Such endogenously expressed TGF-$\beta$1 is sufficient to arrest cell division if cultured in the presence of single growth factors that have been identified as survival factors for single LTR-HSC (Li and Johnson, Blood 15;84(2):408–14, 1994; Ploemacher R E et al. Stem Cells 11:336–347, 1993). In addition, greater than 90% of LTR-HSC clones exhibited a high proliferative potential (HPP), which is defined as clones able to attain greater than 100,000 cells by day 14 of culture in response to SCF, IL-6 and IL-3; and are generally characterized by: (1) a relative resistance to treatment in vivo with the cytotoxic drug 5-fluorouracil; (2) a high correlation with cells capable of repopulating the bone marrow of lethally irradiated mice; (3) their ability to generate cells of the macrophage, granulocyte, megakaryocyte and erythroid lineages, and (4) their multifactor responsiveness. (See, e.g., McNiece, I. K., *Int J Cell Cloning* 8(3):146–60, 1990).

In general, LTR-HSC do not survive in culture without cell division and/or differentiation and the survival of single LTR-HSC cultured in medium alone (without exogenously provided cytokines) is limited to a few days. The results presented herein demonstrate that exposure of highly purified LTR-HSC to a neutralizing anti-TGF-beta antibody (e.g., ID. 11.16, Celltrix Inc.) in the absence of exogenously provided cytokines is effective to promote the survival of such LTR-HSC for up to 18 days in culture without cell division or differentiation. (See Example 2.)

IV. Administration of Murine Anti TGF-$\beta$ Antibody-treated HSC to Mice

The results presented herein further demonstrate that such exposure of highly purified LTR-HSC to a neutralizing anti-TGF-β antibody for a period of time from about 20–180 minutes dramatically reduces the time required for engraftment of LTR-HSC and that such engraftment is sustained on a long term basis. The results of such assays indicate that a substantial proportion of the surviving cells retained their long term repopulating ability. (See Example 2.) These results show that when stem cells are treated with anti-TGF-β antibody for 20 or more minutes prior to in vivo administration, the treated cells acquire the ability to rapidly repopulate the hematopoietic system, a quality typically attributed to short term repopulating cells.

In general, lethally irradiated mice kept under pathogen free conditions will die by about day 12 following lethal irradiation (e.g., at 950 rads), presumably due to a lack of platelets and/or neutrophils. The anti-TGF-beta antibody-treated stem cell compositions and methods described herein provide a means to rescue such lethally irradiated mice by in vivo administration of as few as about 60 anti-TGF-beta antibody-treated stem cells, which upon in vivo administration results in 100% survival of lethally irradiated mice at day 12 following lethal irradiation.

A demonstrable anti-TGF-beta antibody effect requires a cell preparation enriched for LTR-HSC and cannot be seen by anti-TGF-beta antibody treatment of unfractionated bone marrow or any other cell population which contains substantial numbers of short term repopulating cells, along with the long-term repopulating cells.

V. In vitro Treatment Of Baboon HSC with Anti TGF-β Antibodies

Due to the genetic similarities between primates and humans, primates are an attractive model for the study of human hematopoiesis. In previous studies, when baboon bone marrow was treated in vitro with recombinant human stem cell factor (SCF or c-kit ligand), SCF alone had little effect on the growth of hematopoietic colony-forming cells but the number of colonies formed in response to erythropoietin (Epo), interleukin-3 (IL-3), and granulocyte-macrophage colony-stimulating factor (GM-CSF) did increase suggesting an increase in hematopoiesis. This was confirmed when SCF, administered in vivo, resulted in an increase in the number of erythrocytes, neutrophils, lymphocytes, monocytes, eosinophils, and basophils in the peripheral blood and an increase in the cellularity and the number of colony-forming unit-granulocyte-monocyte (CFU-GM) and burst-forming unit-erythroid (BFU-E) cells in bone marrow (Andrews R G et al., Blood Oct. 15, 1991; 78(8):1975–80).

Culture systems are under development for the expansion of primate HSCs that retain functional attributes of HSC and for gene transfer into CD34-enriched baboon marrow repopulating cells. (See, e.g., Medin J A et al., Ann N Y Acad Sci Apr. 30, 1999;872:233–40 and Kiem H P et al., Blood Sep. 15, 1998;92(6): 1878–86.)

As detailed in Example 3, when approximately 100, 50 or 25 baboon lin-CD34+ cells, characterized and sorted by FACS, were treated with monoclonal anti-TGF-β antibody (ID11.16, Celltrix Inc.) in the absence of exogenously provided cytokines, for a time period of 7 days, the proportion of surviving cells and the percentage of wells with viable blast cells was increased relative to lin-CD34+ cells treated with the isotype control antibody, IgG1K. (See also FIG. 4.)

In addition, when single cells of the above phenotype were cultured in the presence of anti-TGF-β antipody, the percentage of viable cells at days 7 and 14 was also increased relative to cell treated with the isotype control antibody, IgG1K.

VI. In vitro Treatment of Human HSC with Anti TGF-β Antibodies

The culture of human adult hematopoietic stem cells under conditions containing exogenously provided cytokines and an agent effective to block TGF-β, has been observed to result in an increase in multipotent progenitor cells in a short term culture assay relative to cells cultured in the absence of such an anti-TGF-β1 agent.

More recently, it has been shown that the expression of FLT3 and the IL6 receptor (IL6-R) is decreased by TGF-β1 but rapidly up-regulated by anti-TGF-β1 (Fortunel N et al., Cell Sci July 1998;111 (Pt 13): 1867–75). When purified human stem cells characterized as CD34+ Thy1+ were cultured in the presence of a neutralizing antibody against TGF-β1, the percentage of cycling cells, proliferation, and absolute number of clonogenic progenitors increased in relative to cultures which were not treated with anti-TGF-β antibody (Imbert A M et al., Exp Hematol May 1998;26(5):374–81).

As detailed in Example 4, when human HSC, characterized by FACS analysis as CD34+ CD38$^{low}$ were treated with monoclonal anti-TGF-β blocking antibody (ID11.16, Celltrix Inc.) in the presence of cytokines, for a time period as short as 6 hours, a greater number of CFU-C colonies, a greater number of HPP clones with more than 100,000 cells, increased c-kit expression and an increased number of cells that are actively cycling were detected, confirming that the addition of anti-TGF-β antibody to cultures of human HSC releases multipotent progenitors from quiescence with a significantly higher hematopoietic potential than those activated by cytokines alone.

VII. Methods and Compositions of the Invention

Transplantation of hematopoietic stem cells derived from peripheral blood and/or bone marrow is increasingly used in combination with chemotherapy and/or radiation therapy for the treatment of a variety of disorders including numerous forms of cancer. The percentage of cells in such cell preparations that are capable of rapid and/or long-term hematopoietic reconstitution is very low. In addition, due to the lack of a culture system for in vitro or ex vivo preservation of stem cells, once obtained, stem cell preparations are typically frozen in liquid nitrogen until used. Upon thawing, the viability and number of stem cells is further reduced. Therefore, a need exists to develop a means to preserve stem cells in vitro or ex vivo following enrichment and to facilitate rapid expansion of the cells following in vivo administration to a subject or in vitro transfer to culture conditions effective to promote expansion and/or differentiation.

Many cancer treatment regimens, result in immunosuppression of the patient, leaving the patient unable to defend against infection. Supportive care for immunosuppression may include protective isolation of the patient, such that the patient is not exposed to infectious agents, administration of: antibiotics, antiviral agents and antifungal agents; and/or periodic blood transfusions to treat anemia, thrombocytopenia (low platelet count), or neutropenia (low neutrophil count).

Current transplantation regimens that employ cell populations enriched for hematopoietic stem cells and/or bone marrow transplantation also suffer from an excessive lag time between transplantation and repopulation of the patient's hematopoietic system, in particular patients often suffer from a deficiency in neutrophils and platelets.

Neutrophils are involved in defending the host against infection. Frequently, following a chemotherapy or radiation therapy, a patient will suffer from insufficient neutrophil counts for time period of from about 3 to 4 weeks, or a longer time period resulting in increased susceptibility to infection.

Platelets are necessary for effective blood clotting at a site of injury. Frequently, following chemotherapy, radiation therapy, transplantation of a cell population enriched for hematopoietic stem cells or bone marrow transplantation, a patient will suffer from an insufficient platelet count for a time period of from about 4 to 6 weeks, or a longer time period resulting in the patient being easily bruised and excessive bleeding.

The invention is based on the discovery that culture of stem cells in the presence of anti TGF-β antibodies is effective to result in both maintenance of cells having the phenotype and function of stem cells for an extended time in culture (e.g., at 37° C. or 4° C.), without cell division or differentiation, and the ability of such cells to provide rapid and sustained repopulation of the hematopoietic system of a host following in vivo administration or rapid expansion and differentiation of such stem cells following transfer to in vitro culture conditions effective to result in such expansion and/or differentiation.

While the mechanism is not part of the invention, it will be understood that such rapid stem cell expansion following treatment with anti TGF-β antibodies implies that the number of stem cells is also increased by treatment with anti TGF-β antibodies.

Culture conditions for maintenance of stem cells by treatment with anti TGF-β antibodies are described herein. However, it will be understood that the optimal survival of stem cells is dependent upon the amount and type of anti TGF-β antibody added to the culture, the time of exposure thereto and the purity and source of the stem cells (i.e., bone marrow, mobilized peripheral blood or cord blood (murine versus human), or human fetal liver.

In one aspect, the invention provides hematopoietic stem cells that are preserved in culture at 37° C. or 4° C., following treatment with anti TGF-β antibodies. Such a hematopoietic stem cell composition finds utility in a variety of applications, including, but not limited to, preserving a population of hematopoietic stem cells ex vivo for subsequent in vivo administration to a subject for purposes of (1) rapid and sustained hematopoietic stem cell replacement therapy, (2) reducing the immune response to allogeneic transplants (ie, GVHD), (3) treatment of autoimmune disease; (4) gene therapy and (5) treatment of HIV-infection in a subject.

Once an anti TGF-β antibody-treated stem cell composition is prepared, the cells may be maintained in culture at 37° C. or 4° C. for at least 14 days without cell division or differentiation. In general, such an anti TGF-β antibody-treated stem cell composition is maintained in culture until use.

However, the calls may be frozen in liquid nitrogen and stored for long periods of time, using standard conditions, such that they can later be thawed and used, e.g., for administration to a patient. The cells will usually be stored in a typical freezing medium, e.g., 10% DMSO, 50% fetal calf serum (FCS), and 40% cell culture medium.

Autologous hematopoietic stem cell transplantation has been used to treat many solid tumors, including but not limited to, breast cancer and ovarian cancer. Prior to hematopoietic stem cell transplantation the patient may or may not receive a chemotherapy regimen to reduce the amount of tumor present, generally followed by: (1) the collection of the patient's hematopoietic stem cells from either bone marrow or mobilized peripheral blood, (2) culture of hematopoietic stem cells in the presence of cytokines or cryopreservation in liquid nitrogen, (3) high-dose chemotherapy administration intravenously (in most cases), and (4) reinfusion of the patient's hematopoietic stem cells (IV), approximately 48 hours after the chemotherapy administration is complete, and (5) further treatment of the patient with growth factors to promote the differentiation of the hematopoietic stem cells and repopulation of the patients hematopoietic system. In general, during this time the patient is immunocompromised and protective isolation is required.

Allogeneic hematopoietic stem cell transplantation has been used to treat patients with leukemia, aplastic anemia, lymphomas (Hodgkin's disease and non-Hodgkin's lymphoma), and immune deficiency diseases. An allogeneic hematopoietic stem cell transplantation protocol is similar to that used for autologous transplantation with the exception that in allogeneic transplantation, the donor and recipient must be matched based on the similarity of HLA cell surface antigens in order to minimize the immune response of both donor and recipient cells against the other.

Graft Versus Host Disease (GVHD)

GVHD is a frequent complication of allogeneic transplantation. About half of the patients undergoing an allogeneic bone marrow transplant develop some GVHD, which is generally mild, but can be life threatening in some cases. In GVHD, the donor's cells attack the recipient's organs and tissue. Patients with GVHD have an increased susceptibility to infection and the skin, liver, and gastrointestinal tract may be attacked in GVHD.

GVHD is caused by T-cells, which recognize the patient's cells as being foreign. T-cells are able recognize differences based on human leukocyte antigens (HLA). Even when the donor and recipient have similar HLA types, many minor markers differ between them except when the donor and recipient are identical twins. Hence, graft versus host disease (GVHD) is a potential problem and treatment to minimize the GVH response is part of the therapeutic regimen for most transplants.

In the case of hematopoietic stem cell transplantation, such treatment often includes, T-cell depletion (i.e., by elutriation which removes T-cells based on density gradient centrifugation) alone, or in combination with hematopoietic stem cell enrichment by selection using monoclonal antibodies with hematopoietic stem cell markers, and drug therapy for prevention of GVHD, e.g., by administration of cyclosporine (an immunosuppressive drug), alone or together with mehtotrexate.

In one aspect, the culture of hematopoietic stem cells under conditions described herein results in a hematopoietic stem cell composition that results in rapid and sustained repopulation of the hematopoietic system of the subject following readministration.

Stem cells within such an ex vivo expanded stem cell composition lack immunological memory of self and non-self antigens, such that transplantation of the hematopoietic stem cells into an allogeneic host is unlikely to result in GVHD.

One exemplary therapeutic regimen involves ex vivo culture of stem cells derived from a cancer patient in the presence of anti TGF-β antibodies, wherein stem cells are purified from an stem cells-containing cell population taken from the patient in a manner effective to eliminate cancer-containing cells and the cells are cultured under the conditions described herein such that the number of viable cancer-free stem cells are maintained in culture at 37° C. or 4° C. for a period of 14 or more days. This is followed by reinfusion of the anti TGF-β treated stem cell composition into the patient resulting in rapid and sustained repopulation of the hematopoietic system of the patient by about 1–3 weeks post-transplant. In many cases, the therapeutic regimen also includes additional intervention such as radiation therapy and/or chemotherapy. The treatment may occur prior to, during or subsequent to re-infusion of ex vivo expanded stem cells.

Autoimmune Disease

As hematopoietic stem cells differentiate they are exposed to the various antigens present on the cells and tissue of the host and immunological tolerance is established during T cell development within the thymus. In general, T cells that would be reactive to host proteins do not survive. However, in some cases, the immune system may recognize self antigens as foreign resulting in an immune reaction against one or more endogenous antigens, leading to an autoimmune condition or disease.

Exemplary autoimmune conditions include organ specific forms wherein the immune response is directed against, e.g., the cells of the adrenal glands, causing Addison's disease, against the thyroid causing auto-immune thyroiditis (Hashimoto's disease) or against the beta cells of the islets of Langerhans in the pancreas, resulting in insulin-dependent diabetes mellitus; and non-specific forms wherein the immune response is directed against an antigen that is ubiquitous, e.g., an immune reaction against DNA, resulting in the disease systemic lupus erythematosus. Further examples include, Sjögren's syndrome, caused by the production of auto-antibodies against salivary ducts, rheumatoid arthritis. Autoimmunity may be the result of attack by antibodies, T-cells or both.

The invention provides methods and compositions for the treatment of autoinmmune disease. In such methods, stem cells are obtained from a patient, followed by treatment of the patient with chemotherapy, radiation therapy or other means to deplete the patient of residual T-cells. The patients' stem cells or stem cells from an allogeneic donor are cultured ex vivo in the presence of anti TGF-β antibodies resulting in maintenance of viable stem cells in vitro at 37° C. or 4° C. for a period of at least 14 days, followed by reinfusion of the anti TGF-β-treated stem cell composition into the patient resulting in repopulation of the hematopoietic system of the patient by about 1–3 weeks post transplantation. As the stem cells develop in the presence of the antigenic repertoire of the host, the newly developed T-cells should not recognize host antigens as foreign and GVHD should not occur.

Such an in vitro anti TGF-β antibody-treated hematopoietic stem cell composition lacks immunological memory of self antigens, such that transplantation of the stem cell composition finds utility in transplantation regimens for treatment of a patient with an autoimmune disease, in order to minimize or eliminate the autoimmune condition.

It will be understood that such ex vivo hematopoietic stem cell treatment and re-infusion is generally used in combination with additional therapeutic intervention to minimize the autoimnmune response of the patent's cells which are present prior to and during hematopoietic stem cell isolation and in vitro stem cell anti TGF-β antibody treatment. Such additional treatment components include compositions and procedures known in the art for the treatment of autoimmune disease.

Gene Therapy Applications

Gene therapy is a fast evolving area of medical and clinical research. Gene therapy encompasses gene correction therapy, and transfer of therapeutic genes and is being applied for treatment of cancer, infectious diseases, multigenic diseases, and acquired diseases.

Exemplary disease targets include, but are not limited to cancer such as prostate cancer, breast cancer, lung cancer, colorectal cancer, melanoma and leukemia; infectious diseases, such as HIV, monogenic diseases such as CF, hemophilia, phenylketonuria, ADA, familial hypercholesterolemia, and multigenic diseases, such as restenosis, ischemia, and diabetes.

Given that hematopoietic stem cells have been demonstrated to be capable of maintaining their numbers in vivo without exhaustion, can repopulate at least the entire hematopoietic system and that mature blood cells circulate throughout the body where a corrected gene product needs to be delivered or a corrected gene product would cure a particular deficiency (e.g., adenosine deaminase deficiency), stem cells are an optimal vehicle for gene therapy.

The challenge of gene transfer into stem cells using retroviral vectors has been twofold: (1) cell division of stem dells is required for proviral integration to occur (2) during stem cell division self-replication and not differentiation must be achieved. The present discovery provides a means to achieve both requirements.

Cell transduction is possible in vivo, however, it is simpler and more easily controlled ex vivo or in vitro, rendering ex vivo cultured hematopoietic stem cells extremely useful for therapeutic gene therapy. (See, e.g., Beutler E, *Biol Blood Marrow Transplant* 5(5):273–6, 1999; Dao M, Leukemia 13(10):1473–80, 1999.)

An exemplary therapeutic gene therapy regimen may include the steps of obtaining a source of stem cells from a subject, stem cell enrichment or purification, in vitro or ex vivo stem cell expansion, transduction of stem cells with a vector containing a gene of interest, and reintroduction into a subject.

The anti-TGF-β antibody treated stem cells described herein provide a means to genetically modify stem cells under conditions lacking exogenously provided cytokines.

The transfer of genetic material into cells can be achieved by physical and chemical methods or by the use of recombinant viruses. In the case of ex vivo transfer, chemical and physical methods such as calcium phosphate, electroporation and pressure mediated transfer of genetic material into cells are often used. Several recombinant viral vectors which have been used for effective delivery of genes into mammalian cells include viral vectors, for example, retroviral vectors, adenovirus vectors, adenovirus-associated vectors (AAV), herpes virus vectors, pox virus vectors; non-viral vectors, for example naked DNA delivered via liposomes, receptor-mediated delivery, calcium phosphate transfection, electroporation, particle bombardment (gene gun), or pressure-mediated gene delivery. Various reports have been presented regarding the efficacy of gene therapy for the treatment of monogenic diseases, early stage tumors, and cardiovascular disease. (See, e.g., Blaese R M, et al., Science 270, 475–480, 1995; Wingo P A, et al., Cancer 82(6), 1197–1207, 1998; Dzau V, Keystone Symposium Molecular and Cellular Biology of Gene Therapy, Keystone, Colo. Jan. 19–25, 1998; and Isner J, Keystone Symposium Molecular and Cellular Biology of Gene Therapy, Keystone, Colo. Jan. 19–25, 1998.)

Characterizing Stem Cell Compositions

The stem cell compositions described herein, may be evaluated, e.g., by conventional FACS assays for the phenotype of cells produced by in vitro culture or at various time points after in vivo administration of stem cells.

Phenotypic analysis is generally carried out using monoclonal antibodies specific to the cell type being analyzed. The use of monoclonal antibodies in such phenotypic analyses is routinely employed by those of skill in the art for cellular analyses.

Hematopoietic stem cells are characterized phenotypically as detailed above. Such phenotypic analyses are generally carried out in conjunction with biological (functional) assays for a given cell type of interest, for example; (1) hematopoietic stem cells, LTCIC, cobblestone forming assays, and assays for HPP-CFC; (2) granulocytes or neutrophils, clonal agar or methylcellulose assays wherein the medium contains G-CSF or GM-CSF; (3) megakaryocytes, clonal agar or methyl cellulose assays wherein the medium contains Tpo, IL-3, IL-6 and IL-11; and (4) erythroid cells, clonal agar or methyl cellulose assays wherein the medium contains EPO and SCF or EPO, SCF and IL-3.

It will be understood that the exact nature of such phenotypic and biological assays will vary dependent upon various factors, including the source and degree of purity of the stem cell composition under evaluation.

In cases where a subject has been diagnosed as having a particular type of cancer, autoimmune disease or other disease condition, the status of the condition is also monitored using diagnostic techniques appropriate to the condition under treatment.

VIII. Utility

The hematopoietic stem cell compositions described herein find utility in a variety of applications. For example, an in vitro or ex vivo stem cell composition which has been treated with anti-TGF-beta monoclonal antibodies serves as a source of cells for rapid repopulation of a subject following in vivo administration and for rapid in vitro expansion/differentiation following transfer to the appropriate culture conditions. In addition, such anti-TGF-beta antibody treated stem cells provide a source of stem cells for various cellular transplantation and gene therapy applications.

Anti-TGF-beta antibody treated stem cells also find utility in repopulating non-hematopoietic tissues in vivo, including, but not limited to liver. Further uses include the use of anti-TGF-beta treated stem cells to initiate in vitro cultures of expanded and/or differentiated stem cells for any of a number of uses for which clinicians currently rely on cell preparation containing small numbers of stem cells which must be used soon after they are prepared.

Such an in vitro or ex vivo anti-TGF-beta antibody treated stem cell compositions also finds utility in both autologous and allogeneic hematopoietic engraftment when readministered to a patient, where the cells are freed of neoplastic disease and graft-versus-host disease can be avoided.

Alternatively, such an in vitro or ex vivo anti-TGF-beta antibody treated stem cell composition may be used for gene therapy to treat any of a number of diseases. In such cases, genetically modified stem cells containing a transgene of interest, e.g., directed toward a particular disease target, are prepared in vitro and reinfused into a subject such that the cell type(s) targeted by the disease are rapidly repopulated by differentiation of cells in the stem cell composition following reinfusion into the subject.

All patent and literature references cited in the present specification are hereby incorporated by reference in their entirety.

The following examples illustrate but are not intended in any way to limit the invention.

Materials and Methods

Murine HSC Preparation and Culture with Antibodies

In general, murine LTR-HSC were purified from B6SJL mice (CD45.1+) by flushing cells from femurs of male B6.SJL-Ptprc$^a$ Pep3$^b$/BoyJ (Ly5.1) (CD45.1) (B6.SJL) mice (Jackson Labs, Bar Harbor, Me.) with medium consisting of IMDM medium (Gibco BRL Life Technologies, Gaithersburg, Md.) supplemented with 20% heat-inactivated defmed horse serum (HyClone Laboratories, Logan, Utah), 100 units/ml penicillin-10 µg/ml streptomycin, 2 mM L-glutamine. Low density cells are enriched using 1.080 g/ml Nycodenz separation medium (Nycomed Pharma AS OSLO, Norway), followed by isolation of the lin$^-$cell population using Dynal Bead depletion employing lineage-specific monoclonal antibodies. Lin$^-$cells are then incubated with Hoescht 33342 (Ho, final concentration 10 mM) for 1 hr at 37 degrees and Rhodamine 123 (Rh, final concentration 0.1 µg/ml) is added during the final 20 minutes (Wolf, et al., 1993). Cells were then labeled with phycoerythrin (PE)-conjugated anti-c-kit antibody (1 µg/ml final). Finally, propidium iodide (PI) is added (2 µg/ml final concentration) for detection of dead cells and cells are analyzed and sorted by FACS within 1–4 hours. Cell sorting has been performed on a FACStar Plus flow cytometer( or Coulter Elite or Ortho 50) equipped with dual argon lasers, and an automated cell delivery unit (ACDU). Cells are kept chilled at 4° C. with a recirculating water bath. Monochromatic light at 351–364 nm and 488 nm is used for Ho and Rh 123 excitations, respectively. Forward light scatter is detected using 488 bp10 and ND 1.0 filters. Ho emission is detected using a 515 lp filter in order to maximize signals from hematopoietic cells (Goodell et al; Bartelmez et al., unpublished observations). Rh 123 emission was detected using a 530 bp20 filter, PE emission using a 575 bp20 filter, PI emission using a 610 lp filter. Cells were gated using the following steps: first, forward light scatter and PI fluorescence are analyzed and viable cells (PI negative) were selected. Next, gates are set at the various percentages of Rh fluorescence using a 4-log amplifier: the lowest 10% (defined as Rh$^{low}$) and the middle 40% of the peak (defined as Rh$^{high}$). Then Rh$^{low}$ and Rh$^{high}$ cells analyzed for their linear Ho fluorescence and logrithmic PE-anti-c-kit receptor fluorescence. Rh$^{low}$ and Rh$^{high}$ were sorted as individual cells into 96-well plates or collected in bulk.

LTR-HSC enriched in this manner have been intensively characterized and have the following phenotype: "lin-, Rh-123 low, Ho-33342 low, c-kit+, Sca-1+, Thy-1 low, CD-34 negative, AA 4.1 negative" (Bartelmez S, et al., "Functional resolution of hematopoietic long-term and short-term marrow repopulating stem cells in vitro," submitted to *Blood,* 2000).

LTR-HSC, characterized as described above were sorted directly into phosphate buffered saline (PBS) for all experiments in which LTR-HSC were transplanted at time 0 (T=0), or if the cells were to be cultured, the LTR-HSC were sorted directly into basic culture medium for LTR-HSC which generally contains (1) Fisher's medium, 20% horse serum, $10^{-6}$ M hydrocortisone (HC) or (2) IMDM medium plus 12.5% horse serum and 12.5% fetal bovine serum, $10^{-6}$ M hydrocortisone or (3) serum-free medium (QBSF-58, Quality Biological Inc., Gaithersburg. Md.). In PBS or medium containing cultures containing exogenously provided cytokines, the culture medium also contains one or more of interleukin-3,6,11,12 (IL-3,6,11,12), stem cell factor (SCF), or thrombopoietin (Tpo). In other words, in experiments in which cells were directly transplanted prior to short in vitro exposure to anti-TGF-β antibodies, such treatment took place in PBS, not in culture medium.

Antibodies, e.g., anti TGF-β antibodies are added to culture medium at a concentration of from about 0.8–100 μg/ml.

Baboon HSC Preparation and Culture with Antibodies

In general, baboon HSC were purified from bone marrow aspirates. Bone marrow (BM) buffy coat cells were labeled with IgM monoclonal antibody 12–8 (CD34) at 4° C. for 30 minutes, washed, incubated with rat monoclonal antimouse IgM microbeads (Miltenyi Biotec, Auburn, Calif.) for 30 minutes at 4° C., washed, and then separated using an immunomagnetic column technique (Miltenyi Biotec) according to the manufacturer's instructions. The purity of the CD34-enriched cells was between 83% and 97%. The CD 34-enriched cells were then stained with monoclonal antibodies 9.6 (CD2), 51.1 (CD8), and 24.1 (CD10), G17.2 (CD 4) G28.4 (CD40) IF5 (CD20) and 5B12 (an antigen expressed by baboon neutrophils), the cells were washed and stained with anti-murine IgG-FITC conjugated antibodies to detect lineage positive cells and a PE-directly labeled anti-CD34 antibody directed against a different epitope than that recognized by the 12.8 anti CD34 antibody. In this manner, lin-CD34+ cells could be identified and sorted by FACS.

The HSC were characterized by FACS analysis as lin-CD34+ and cultured in IMDM medium containing 12.5% horse serum and 12.5% fetal bovine serum, hydrocortisone and P/S. In cultures containing exogenously provided cytokines, the culture medium also contained one or more of the following purified recombinant human growth factors: SCF, IL-3, 6, G-CSF, GM-CSF, Tpo, and/or erythropoietin (Epo)

Antibodies, e.g., anti TGF-β antibodies are added to culture medium at a concentration of from about 0.8–100 μg/ml.

Human HSC Preparation and Culture with Antibodies

Human HSC were purified from umbilical cord blood samples collected immediately after delivery. However, it will understood that human HSC may be obtained from other sources such as mobilized peripheral blood or bone marrow as further described above. In general, CD34+ cells were purified using of immunomagnetic beads (Dynel), suspended in PBS/BSA (0.2%) and incubated with an anti-CD34 fluorescein isothiocyanate (FITC)-conjugated monoclonal antibody (mAb) (8G 12 clone; Becton Dickinson, San Jose, Calif.) and an anti-CD38 phycoerythrin (PE)-conjugated mAb (HB-7 clone; Becton Dickinson) for 30 minutes at 4° C., then washed twice. Isotype non-specific FITC- and PE-IgG1 were used as negative controls. The $CD38^{low}$ subpopulation was defined as the 10% of CD34+ cells with the lowest intensity of CD38 antigen expression. The CD34+ $CD38^{low}$ cell population was isolated by FACS and deposited into 96-well plates containing medium using a Vantage fluorescence activated cell sorter (FACS; Becton Dickinson) equipped with an automatic cell deposition unit.

HSC were characterized by FACS analysis as the CD34+ $CD38^{low}$ cell population and cultured in semi-solid or liquid medium as further described in Example 4.

In cultures containing exogenously provided cytokines, the culture medium also contained one or more hematopoietic growth factors such as SCF, Tpo, IL-6, TGF-beta, IL-11, IL-12, flt-3, and IL-3. In general, hematopoietic growth factors were purchased from Peprotech, with the exception of TGF-β (Gift of Bristol-Meyers Squibb). Cytokines were used at concentration of 10 ng/ml for IL-6, IL-3, GM-CSF and TGF-β and 50 ng/ml for SCF and flt-3, respectively.

The monoclonal anti-TGF-β blocking antibody (ID11.16, Celltrix Inc.) and the non-blocking 2G1.2 antibody were used at 20 μg/ml.

Immunophenotyping of LTBMC cells. LTBMC cells were centrifuged and resuspended in 1% (w/v) bovine serum albumin in Dulbecco's phosphate-buffered saline. Fluorochrome-conjugated monoclonal antibodies to various mouse CD antigens, or biotinylated anti-mouse CD34 and FITC- or PE-conjugated strepavidin (Pharmingen, San Diego, Calif.) were incubated with the cells on ice (1 μg antibody/1–2×$10^5$ cells). Cells were washed and analyzed by flow cytometry (FACScan, Becton-Dickinson, Mountain View, Calif.) in the presence of propidium iodide to exclude dead cells.

Clonogenic cell assays. Colony formation assays were performed in soft agar cultures (murine) or methylcellulose (human) in the presence of recombinant cytokines (R & D Systems or PeproTec, Rose Hill, N.J.) (Sitnicka E et al., *Blood* 87, 4998–5005, 1996). Two to five thousand cells were added per ml of culture and plated in 35 mm dishes. Cultures were incubated for 12 days, and colonies were counted using an inverted microscope. In some experiments, cells were plucked from colonies and their morphology assessed after staining with Giemsa. Cytokines were used at the following concentrations: for CFC, 5 ng/ml mouse GM-CSF and 10% (v/v) L929 supernatant (mouse M-CSF); for HPP-CFC, 50 ng/ml rat SCF, 20 ng/ml human IL-6, and 10 ng/ml mouse IL-3.

Colony formation assays for murine versus human CFC differ in that human HPP-CFC are carried out in methylcellulose medium (Stem Cell Tech., Cat. No. H4435), in the presence of SCF (50 ng/ml), IL-3 (50 ng/ml), IL-6 (20 ng/ml), erythropoietin (EPO, 1 unit/ml) and GM-CSF (5 ng/ml). (See, e.g., Andrews R G et al., J Exp Med 172(1):355–8, 1990.) LTBMC assay conditions for human cells generally include commercially available media, e.g., Fishers medium; horse serum (Hyclone, Logan, Utah) from a lot selected based on optimal HSC generation in murine Tpo-LTMC assays; purified recombinant human Tpo (rhuTpo, Genentech, South San Francisco, Calif.); hydrocortisone; a human stromal cell component which includes, but is not limited to, cells of mesenchymal origin, including fibroblasts, adipocytes, endothelial cells; and megakaryocytes.

Transplants and competitive repopulation assays. Cells from B6.SJL mice (CD45.1) were harvested, washed, and used unfractionated for transplant. For each test sample, 2–10 recipient C57B16 mice (CD45.2) were irradiated (950 rad, $^{137}$Cesium source) and transplanted by injection via the tail vein with the indicated number of test cells mixed with 4×10$^5$ fresh unfractionated CD45.2 marrow cells. Animals were maintained in microisolator cages in an SPF facility. Peripheral blood samples were obtained by retroorbital bleeding at various times post-transplant. Expression of the donor CD45.1 allele and lineage specific antigens was assessed by two-color flow cytometry analysis of peripheral blood leukocytes using directly labeled monoclonal antibodies as described above for cultured cells. The frequency of long-term repopulating units was estimated using the maximum likelihood model that requires limiting dilution cell transplants of the test cells (Taswell C., *J Immunol* 126, 1614–9, 1981).

In vivo assays for human HSC. In vivo assays for human HSC may be carried out by using approximately 10,000–20,000 purified lineage negative CD34+ cells derived from culture in an in utero fetal sheep assay (Zanjani ED et al., *Stem Cells* 13(2):101–11, 1995).

EXAMPLE 1

Maintenance of Murine LTR-HSC in vitro Following Treatment with Anti-TGF-beta Mab
Single Cell Studies in the Absence of Exogenously Provided Cytokines: HSC Survival Detected by Viability and HPP (Macroclone) Assay Anti-TGF-β antibody treatment of single LTR-HSC cultured in the absence of exogenously supplied cytokines resulted in survival of a high proportion of cells up to 18 days as single cells compared to LTR-HSC cultured in medium alone in which single cell survival was limited to a few days. FIG. 1 depicts the survival of single sorted LTR-HSC as indicated by the number of HSC per well counted on day 0, 1, 3, 4, 5, 6, 7, 10, 11, 14, and 18 when incubated in medium alone or in medium containing 0.8–100 µg/ml anti-TGF-β1 neutralizing antibody (ID.11.16, Celltrix Inc.), indicating that greater than 3-fold more HSC survived at least 14 days in medium containing 20 µg/ml of the anti-TGF-β1 neutralizing antibody relative to HSC incubated in medium alone. The observed survival effect was dependent on the concentration of the anti-TGF-β1 neutralizing antibody.

Following such treatment, essentially all single cells began cell division synchronously and formed macroclones upon the addition of a combination of cytokines, SCF+IL-3+IL-6, which not only reflects the maintenance of their high proliferative potential (a characteristic of murine HSC) but also suggests that the cells became synchronized in respect to cell cycle entry (in contrast to freshly isolated LTR-HSC that are heterogeneous with respect to the time required to enter the cell cycle).

Multiple Cell Studies in the Absence of Exogenously Provided Cytokines: HSC Survival Detected by Transplantation Assay 100 LTR-HSC were cultured without growth factors but in the presence of α-TGF-β1, for 5 days, then assayed in a competitive repopulation assay, as detailed above. The results indicate that a substantial proportion of the surviving cells retained their LTR ability (Table 2, below). In this experiment, LTR-HSC were directly FACS sorted into 96-well plates at 100 cells/well containing medium plus either α-TGF-β1 neutralizing antibody (ID.11.16, Celltrix Inc.) or isotype control antibody IgG1K at a final concentration of 20 µg/ml. After 5 days, the cells were counted, assayed for HPP formation in agar and transplanted together with 3×10$^5$ support cells into lethally irradiated recipients. The recipient animals were analyzed for the presence of donor type cells in the peripheral blood by FACS analysis. The results suggest that anti TGF-β1 antibody treatment promotes the survival of the LTR-HSC.

TABLE 2

The effect of α-TGF-β1 on in vitro survival and in vivo repopulation capability of Rh$^{low}$ cells.

| Conditions | Viable Cells per Mouse | HPP/ Mouse | % Donor Repopulation (1.5 months post-trans.) | % Donor Repopulation (10.5 months post-trans.) |
|---|---|---|---|---|
| 100 Rh$^{low}$ cells (5d culture in medium + isotype control Ab) | 0.8 ± 0.8 | 0 | 0 | 0 |
| 100 Rh$^{low}$ cells (5d culture in medium + α-TGF-β1, ID.11.16) | 40 ± 6 | 33 ± 5 | 25 ± 20 | 22 ± 17 |

EXAMPLE 2

Rapid in vivo Repopulation of Murine LTR-HSC Following in vitro Treatment with Anti-TGF-beta Mab In one experiment, LTR-HSC were purified from B6SJL mice (CD45.1+); and incubated ex vivo for 1 hour in either culture medium alone or culture medium containing mouse α-TGF-β neutralizing antibodies (ID11.16, Celltrix Inc.), in the absence of exogenously supplied cytokines.

The antibody-treated LTR-HSC were then transplanted into lethally irradiated congenic strain C57B16 (CD45.2)

mice along with 400,000 unfractionated bone marrow competitor cells (CD45.2). Donor derived neutrophils, peripheral blood B lymphocytes and peripheral blood T lymphocytes were quantitated by FACS analysis.

The results of a representative experiment are shown below in Table 3, and indicate that LTR-HSC treated with α-TGF-β1 antibodies for 1 hour in the absence of exogenously provided growth factors, rapidly and substantially engraft lethally irradiated recipients. The results indicate that the greater degree of early donor engraftment by α-TGF-β1 treated LTR-HSC is primarily due to the rapid production of donor neutrophils in the transplanted recipient.

Figure 3:
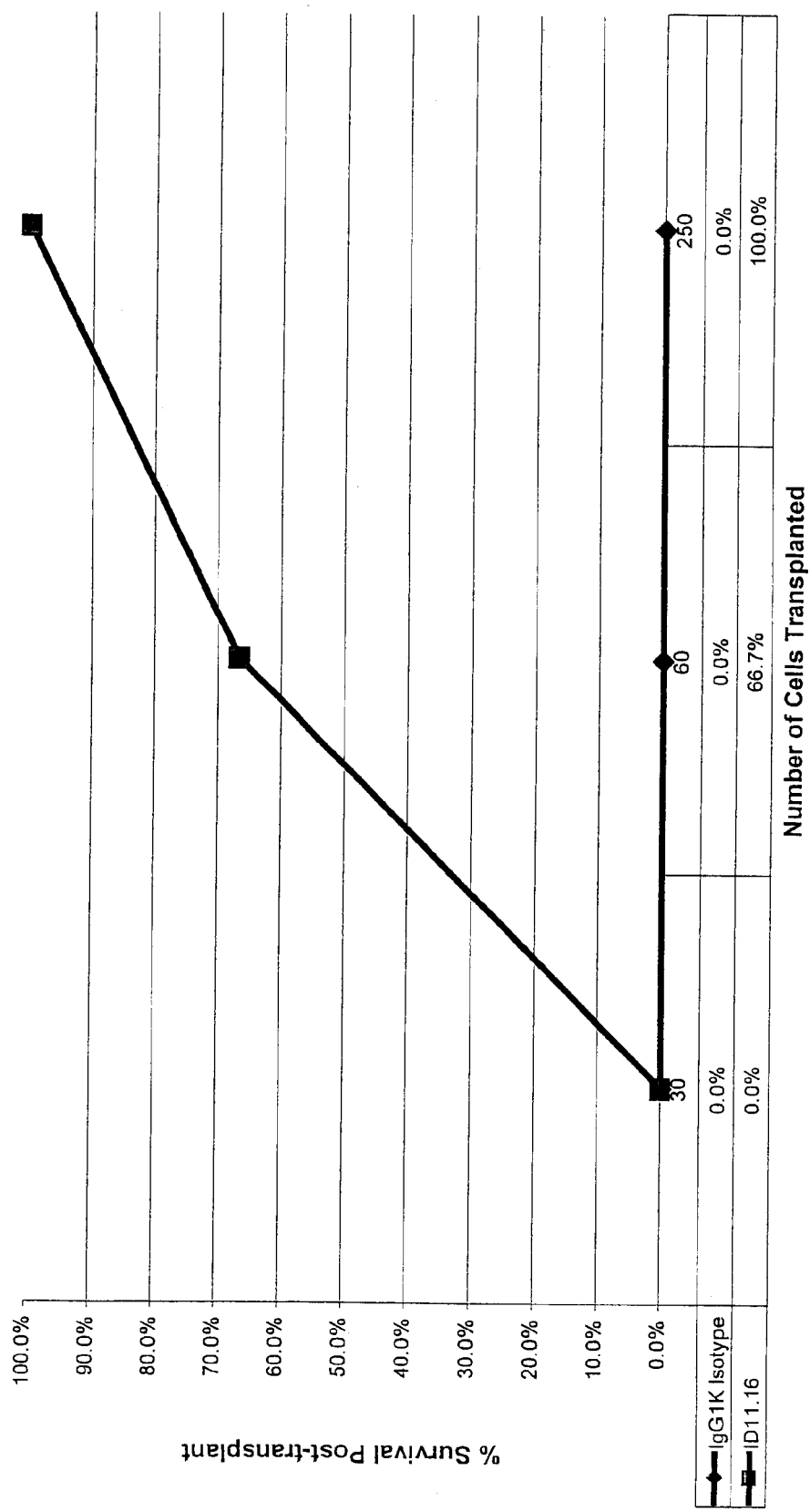
FIG. 3 shows the % survival of lethally irradiated mice following transplantation of LTR-HSC treated with either anti-TGF-β1 neutralizing antibody (ID.11.16) or IgG1K isotype control antibody.

The percent post-transplantation survival was evaluated 30 days later, as shown in FIG. 3. When as many as 250 LTR-HSC were treated with IgG1K isotype control antibody prior to transplantation none of the mice survived. In contrast, when 60 or 250 LTR-HSC were treated with neutralizing α-TGF-β1 antibody (ID11.16, Celltrix Inc.) prior to transplantation, approximately 65% or 100% of the mice survived, respectively.

Consistent with these results, transplantation of single LTR-HSC treated with neutralizing α-TGF-β1 antibody (ID11.16, Celltrix Inc.) into lethally irradiated mice resulted in engraftment in greater than 80% of the mice that received transplants. The rapid engraftment of LTR-HSC did not

TABLE 3

[2]In vivo repopulation of murine LTR-HSC following in vitro treatment with anti-TGF-beta Mab.

| Treatment | Time post-transplant | Number of transplanted cells | % donor cells | % donor neutrophils | % donor B lymphocytes | % donor T lymphocytes |
|---|---|---|---|---|---|---|
| day 0-#1 (none) | 4 weeks | 100 ± 12 | 2 ± 1 (2) | 0 (2) | 82 ± 25 (2) | 18 ± 25 (2) |
| day 0 #1 (medium + α-TGF-β1 Ab for 1 h) | 4 weeks | 100 ± 12 | 42 ± 8 (4) | 92 ± 5 (4) | 7 ± 3 (4) | 1 ± 2.1 (4) |

[2]The results are presented as mean ± standard error (SE) and the number of is indicated in parentheses ().

In further experiments LTR-HSC were purified from B6SJL mice (CD45.1+); and treated ex vivo for varying lengths of time with one of a number of types of antibodies including (a) mouse anti-TGF-beta neutralizing antibodies (b) non-neutralizing (but TGF-beta binding) antibodies, (c) isotype control antibodies, (d) antibodies known to bind to LTR-HSC, but not to TGF-beta (i.e., antibodies to c-kit, Sca-1, or CD45). The antibody-treated LTR-HSC were then transplanted into the congenic strain C57B16 (CD45.2) along with 400,000 unfractionated competitor cells (CD45.2) and donor derived peripheral blood T-cells, B-cells, monocytes and neutrophils were assayed by FACS analysis and total cell counts were performed.

Figure 2:
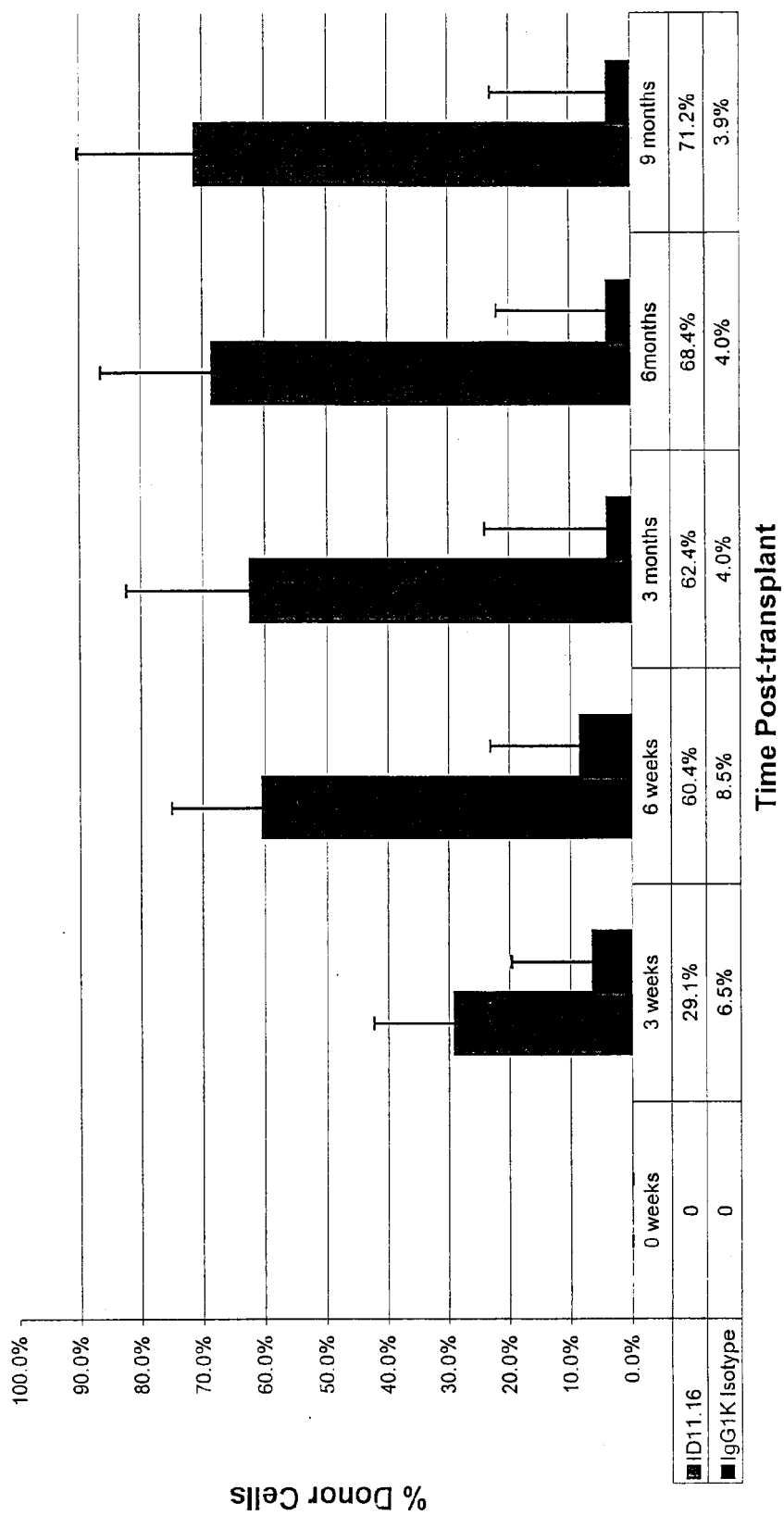
FIG. 2 shows the relative repopulation lethally irradiated mice with LTR-HSC treated with either TGF-β1 neutralizing antibody, ID.11.16 or IgG1K isotype control antibody, at various time points up to 9 months post-transplant.

By way of example, when LTR-HSC were treated with an IgG1K isotype control antibody, the engraftment of 100 LTR-HSC occurred slowly, such that at 9 months post-transplant only 3.9% of the cells in the peripheral blood were donor-derived CD45.1+ cells. (See FIG. 2.)

In contrast, when LTR-HSC were treated with α-TGF-β1 neutralizing antibody (ID.11.16, Celltrix Inc.) for 20–120 minutes the cells rapidly engrafted to reach greater than 30% donor cells by 3 weeks with sustained engraftment for at least 9 months. Again, early engraftment was predominately donor neutrophils followed by B-cells and then T-cells by 1.5 months. The results show that the HSC transferred into the mice not only were able to rapidly repopulate the animals, but also were capable of sustained repopulation characteristic of LTR-HSC. (See FIG. 2.)

In the next example, experiments are described where LTR-HSC were treated with neutralizing α-TGF-β1 antibody (ID11.16, Celltrix Inc.) for 20 to 120 minutes and transplanted into lethally irradiated mice (950 rads) without support marrow in order to test the ability LTR-HSC to rescue lethally irradiated mice directly through a mechanism of rapid repopulation in which donor platelets and neutrophils are produced usually within the first 1.5 weeks post transplant.

impair the long term repopulating ability as measured by a sustained high percentage of donor chimeras after greater than 6 months post-transplant.

EXAMPLE 3

Maintenance of Baboon LTR-HSC in vitro Following Treatment with Anti-TGF-beta Mab The effect of α-TGB-β antibody on baboon LTR-HSC cultured under standard conditions was evaluated using baboon lin-CD34+ cells prepared as described above. These compositions are enriched for both STR- and LTR-HSC. Groups of approximately 100, 50 or 25 lin-CD34+ cells were directly deposited following FACS sorting into 96 well plates containing IMDM medium supplemented 12.5% FBS and 12.5% HS, HC and P/S and anti-TGF-β1 antibody ID11 or IgG1K without exogenously provided growth factors and incubated continuously in the presence of the antibodies. The results presented in Table 4 indicate that indicate that treatment of CD34+ baboon cells with anti-TGF-β1 antibody in the absence of added growth factors is effective to increase the proportion of surviving cells and the percentage of wells with viable blasts at day 7 relative to CD34+ cells treated with the isotype control antibody, IgG1K. These results indicate that anti-TGF-β1 antibody ID11 promotes the survival of primitive baboon hematopoietic cells similar to the effect observed when murine LTR-HSC are treated with anti-TGF-β1 antibodies.

TABLE 4

Lin-CD34 + baboon cells cultured in the absence of added growth factors: ID11.16, Celltrix Inc. vs. IgG1K isotype

| Conditions | Total number of cells (day 0) | Total number of cells (day 7) | Proportion of surviving cells (day 7) | % positive wells (viable blasts) |
|---|---|---|---|---|
| experiment #1 | | | | |
| medium + isotype control Ab IgG1K (20 µg/ml) | 90 ± 10 | 4 ± 3 | 4% | (3/12) 25% |
| medium + isotype control Ab IgG1K (20 µg/ml) | 42 ± 4 | 4 ± 2 | 9% | (4/12) 33% |
| medium + isotype control Ab IgG1K (20 µg/ml) | 18 ± 3 | 0.7 ± 1.2 | 4% | (1/12) 8% |
| medium + α-TGF-β1 (ID11.16, 20 µg/ml) | 88 ± 8 | 34 ± 17 | 39% | (12/12) 100% |
| medium + α-TGF-β1 (ID11.16, 20 µg/ml) | 38 ± 2 | 18 ± 12 | 47% | (12/12) 100% |
| medium + α-TGF-β1 (ID11.16, 20 µg/ml) | 19 ± 2 | 4 ± 4 | 21% | (6/12) 50% |
| experiment #2 | | | | |
| medium + isotype control Ab IgG1K (20 µg/ml) | 85 ± 9 | 8 ± 7 | 9% | (5/12) 42% |
| medium + isotype control Ab IgG1K (20 µg/ml) | 38 ± 4 | 4 ± 3 | 11% | (3/12) 25% |
| medium + isotype control Ab IgG1K (20 µg/ml) | 19 ± 3 | 0 ± 0 | 3% | (0/12) 0% |
| medium + α-TGF-β1 (ID11.16, 20 µg/ml) | 89 ± 9 | 34 ± 9 | 38% | (10/10) 100% |
| medium + α-TGF-β1 (ID11.16, 20 µg/ml) | 39 ± 2 | 23 ± 13 | 59% | (10/10) 100% |
| medium + α-TGF-β1 (ID11.16, 20 µg/ml) | 19 ± 2 | 4 ± 5 | 21% | (4/10) 40% |

Figure 4:
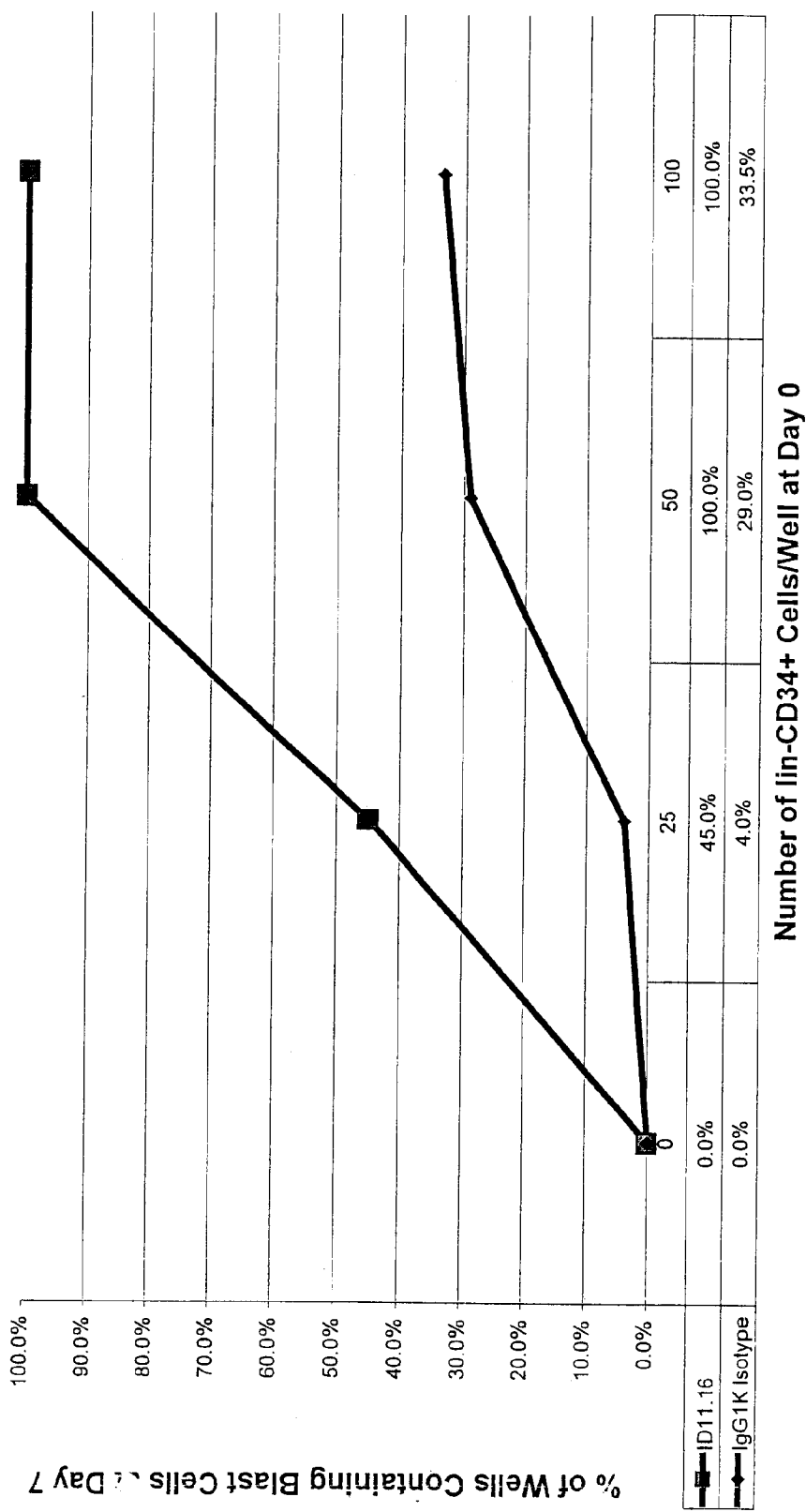
FIG. 4 illustrates the relative survival of blast cells at day 7 following culture of 0, 25, 50 or 100 lin-CD34+ baboon cells in medium containing either anti-TGF-β1 neutralizing antibody (ID.11.16) or IgG1K isotype control antibody in the absence of exogenously provided growth factors.

The relative survival of blast cells at day 7 following initiation of cultures with 0, 25, 50 or 100 lin-CD34+ baboon cells in medium containing either anti-TGF-β1 neutralizing antibody (ID.11.16) or IgG1K isotype control antibody in the absence of exogenously provided growth factors is presented graphically in FIG. 4.

TABLE 5

Effect of anti-TGF-β1 Neutralizing Antibody On The Survival Of Individually Cultured Baboon CD34 + Cells In vitro

| | % of viable single cells and clones | | |
|---|---|---|---|
| Conditions | day 3 | day 7 | day 14 |
| medium alone | 57% | 2% | 0% |
| medium + α-TGF-β1 (ID11.16) | 78% | 28% | 10% |

The data presented in Table 5 show that the effect of the anti-TGF-β1 antibody ID11 or IgG1K is again specific to the anti-TGF-β1 antibody ID11 and is also a direct effect on the enriched baboon cell composition. The survival of single cells was in the order of that observed in the multiple cell cultures.

EXAMPLE 4

Maintenance of Human Stem Cells in vitro Following Treatment with Anti-TGF-beta Mab The effect of α-TGF-β antibody on human stem cells cultured under standard conditions in the was evaluated using human CD34+ CD38$^{low}$ HSC, prepared as described above.

When stem cells were cultured in semi-solid methylcellulose media (Stem Cell Technologies), the media contained IL3, IL6, SCF, GM-CSF and FL plus or minus α-TGB-β antibodies.

Liquid IMDM medium (BioWhitaker) with 20% horse serum was used to culture human stem cells. In general, 100 µl of medium containing IL3, IL6, SF, FL and GM-CSF plus or minus TGF-β or TGF-β antibodies was added to culture wells of 96 well plates on day 0.100 µl of twice concentrated medium containing cytokines was added after 7 and 14 days. In bulk cultures, stem cells were plated at 2×10$^5$ cells/ml in 96-well tissue culture plates (Lux) in 200 µl of complete medium containing cytokines. Depending on the experimental condition, this control medium was supplemented with TGF-β1 or TGF-β1 blocking antibody, as indicated in Table 6.

For clonal studies, the cells in each well were counted using an inverted Leitz Inverted microscope at day 10 and 21. Phenotypic analysis and staining was carried out using cells harvested from 96-well plate cultures. Cells were labeled with FITC-anti-c-kit antibodies (Pharminogen), stained with propidium iodide and stained for cell cycle status, then analyzed using a Vantage flow cytometer. The paired Student's I-test was applied to determine the significance of differences between mean values obtained under each treatment condition.

TABLE 6

The Effect Of Anti-TGF-Beta On Primitive Hematopoietic Progenitor Colony Formation.

| Conditions (media additives) | HPP Colony #[3] | Colony Size | CFU-C Colony # | Colony Size |
|---|---|---|---|---|
| experiment #1 | | | | |
| cytokines | 18 | 100–200 | 59 | 50–100 |
| cytokines + α-TGF-β1 | 39* | 200–400 | 82 | 100–150 |
| cytokines + isotype control Ab | 15 | 100–150 | 63 | 50–100 |
| experiment #2 | | | | |
| cytokines | 7 | 100–150 | 38 | 50–100 |
| cytokines + α-TGF-β1 | 28* | 200–300 | 62 | 100–150 |
| cytokines + isotype control Ab | 8 | 100–150 | 57 | 50–100 |

[3]3 plates counted at day 14: SEM > 10%; *statistically significant P < .05

TABLE 7

The effect of anti-TGF-beta on clonal frequency in single cell assay

| Conditions (media additives) | Number cells per clone[4] | | |
|---|---|---|---|
| | <20,000 | 20,000–100,000 | >100,000 |
| experiment #1 | | | |
| cytokines | 11 | 32 | 7 |
| cytokines + α-TGF-β (continuous)* | 3* | 23 | 25* |
| cytokines + α-TGF-β1 (6 hours) | 4* | 21 | 19* |
| cytokines + isotype control Ab | 10 | 24 | 4 |
| experiment #2 | | | |
| cytokines | 4 | 29 | 2 |
| cytokines + α-TGF-β (continuous)* | 0 | 17 | 11* |
| cytokines + α-TGF-β1 (6 hours) | 1 | 14 | 9* |
| cytokines + isotype control Ab | 3 | 19 | 1 |

[4]plates counted at day 21: SEM > 10%; *statistically significant P > .05

TABLE 8

Effect of anti-TGF-beta antibody on cell-surface c-kit receptor modulation and cell cycle progression.

| Conditions (media additives)[5] | c-kit expression (% cells > 1 log)[6] | Cell cycle | | |
|---|---|---|---|---|
| | | G1 | S | G2M |
| experiment #1 | | | | |
| cytokines | 33.5 | 65 | 28 | 7 |
| cytokines + α-TGF-β | 48.3* | 45 | 39 | 15 |
| cytokines + isotype control Ab | 29 | 67 | 27 | 5 |
| cytokines + TGF-β | 20.7* | 85 | 11 | 4 |

[5]CD34 + CD38$^{low}$ cells were treated in bulk culture for 48 hrs
[6]SEM > 10%; *statistically significant P > .05

The results presented above show that treatment of human CD34+ CD38+ cells with anti-TGF-β antibodies for a time period as short as 6 hours results in a greater number of HPP clones (more than 100,000 cells) and a greater number of CFU-C colonies, plus increased c-kit expression and an increased number of cells that are actively cycling. Thus, addition of anti-TGF-β antibodies to cultures of human HSC stimulated with cytokines releases multipotent progenitors from quiescence with a significantly higher hematopoietic potential than those activated by cytokines alone. In addition, this effect can be accomplished with a 6 hour exposure suggesting that the effect is confined to the initial CD34+ CD38− cells in the culture and not the subsequent daughter cells. Thus the effect appears to be HSC specific and occurs prior to cell division.

In summary, the results presented herein show or suggest that a consistent effect is observed when stem cells isolated from a primary murine, baboon or human source are treated with anti-TGF-beta antibodies.

What is claimed is:

1. A stem cell composition comprising isolated stem cells treated with anti-transforming growth factor beta (TGF-β) antibody under culture conditions that do not result in in vitro replication of said cells.

2. The composition of claim 1, wherein said stem cells are human hematopoietic stem cells characterized as CD34+/ CD38$^{low}$.

3. The composition of claim 1, wherein said stem cells are treated with 0.5 to 100 μg/mL of anti-TGF-β antibody.

* * * * *